United States Patent [19]
Williams et al.

[11] Patent Number: 6,110,925
[45] Date of Patent: Aug. 29, 2000

[54] ANTIBIOTIC FOR METHICILLIN RESISTANT BACTERIA

[75] Inventors: Robert M. Williams, Fort Collins, Colo.; Chenguang Yuan, Skokie, Ill.

[73] Assignee: Research Corporation Technologies, Inc., Tucson, Ariz.

[21] Appl. No.: 09/130,218

[22] Filed: Aug. 6, 1998

Related U.S. Application Data

[60] Provisional application No. 60/054,830, Aug. 7, 1997.

[51] Int. Cl.$^7$ .................. A61D 31/513; C07D 239/22
[52] U.S. Cl. .................. 514/272; 514/86; 544/243; 544/320; 544/321; 548/314.1; 548/465; 564/59; 564/152; 564/155; 564/230; 564/231
[58] Field of Search .................. 544/243, 320, 544/321; 514/86, 272

[56] References Cited

FOREIGN PATENT DOCUMENTS 0 339 596   11/1989   European Pat. Off. .

OTHER PUBLICATIONS

Funabashi Y., et al. "A New Anti–MRSA Dipeptide, TAN–1057A", Tetrahydron, vol. 49, No. 1, 1993, pp. 13–28.
Katayama N., et al. "TAN–1057 A–D, New antibiotics with potent antibacterial activity against methicillin–resistant *Staphylococcus aureus*", J. Antibiot., vol. 46, No. 4, 1993, pp. 606–613.
Yuan C., et al. "Total Synthesis of the Anti Methicillin–Resistant *Staphylococcus aureus* Peptide antibiotics TAN–1057 A–D", J. Am. Chem. Soc., vol. 1997, No. 49, 1997, pp. 11777–11784.
Tian, Z., et al. "Synthesis of optically pure Cα–methyl–arginine", Int. J. Peptide Protein Res., 40, 1992, 119–126.
Yuan C., et al. "An efficient method for the preparation of amidinoureas", Tetrahedron Letters, vol. 37, No. 12, pp. 1945–1948, 1997.

*Primary Examiner*—Makund J. Shah
*Assistant Examiner*—V. Balasubramanian
*Attorney, Agent, or Firm*—Scully, Scott, Murphy & Presser

[57] ABSTRACT

The present invention is directed to anti-bacterial and anti-tumor agents and the synthesis thereof.

36 Claims, No Drawings

ANTIBIOTIC FOR METHICILLIN RESISTANT BACTERIA

This application claims priority from U.S. Provisional Application No. 60/054,830, filed on Aug. 7, 1997.

GOVERNMENT SUPPORT

The invention was made with Government support under Grant No. NSF-CHE-9320010 awarded by the National Science Foundation.

FIELD OF THE INVENTION

The present invention is directed to novel antibiotics useful as therapeutic agents for infectious diseases caused by a pathogenic microorganism, and the production and use thereof.

BACKGROUND OF THE INVENTION

Owing to the development of therapeutics using antibiotics, diseases caused by bacteria have been overcome for the most part. There are, however, still some serious problems to be solved in the field of therapeutics of infectious diseases caused by bacteria. For example, Nosocomial infections caused by methicillin-resistant *Staphylococcus aureas* (MRSA) have become a very serious clinical problem. MRSA has developed resistance to most β-lactam antibiotics as well as numerous other antibiotics due to the presence of the mec A gene. MRSA produces an altered penicillin-binding protein, PBP2a, for which most clinically significant β-lactam antibiotics have low affinity. A desperate search has very recently been initiated to find so-called fourth generation cephalosporins that possess affinity for PBP2a. Screening programs aimed at discovering new structural drug motifs that are efficacious against MRSA have therefore become increasingly significant.

Recently, four new compounds identified as TAN-1057A-D were isolated from Flexibacter sp. PK-74 and PK-176. See, U.S. Pat. No. 4,971,965; Katayama, et al., *The Journal of Antibiotics,* 1993, 606–613 and Funabashi, et al., *Tetrahedron* 1993, 49, 13–28. These have the structures shown hereinbelow.

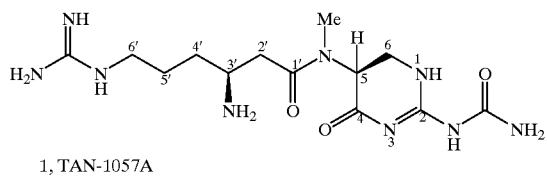

1, TAN-1057A

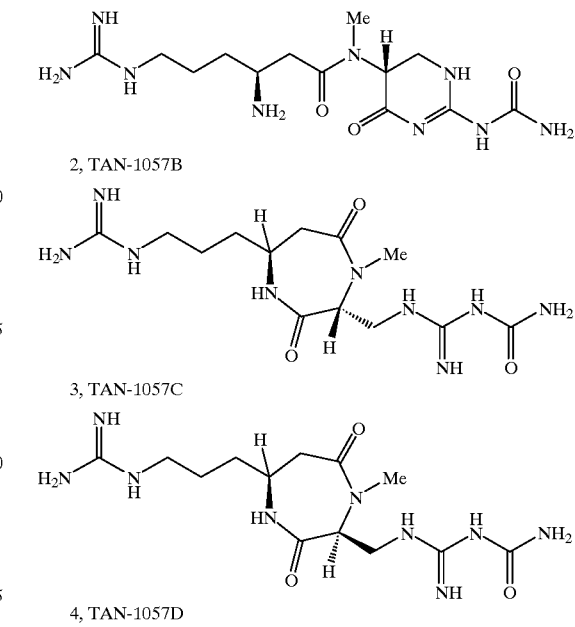

2, TAN-1057B

3, TAN-1057C

4, TAN-1057D

These compounds were found to be dipeptide antibiotics with potent activity against MRSA. TAN-1057A-D displayed better activity against Gram-positive bacteria than against Gram-negative bacteria. TAN-1057A and D, which have the S-configuration in the heterocyclic portion of the molecule, were more active than TAN-1057 B and C which possess the R-configuration. There was no cross-resistance between TAN-1057 and methicillin, erythromycin and gentamycin. TAN-1057A was shown to display potent activity against all of the MRSA strains evaluated and was found to compare very favorably to vancomycin in mice.

TAN-1057A and B are dipeptides consisting of β-homoarginine and a unique heterocyclic amidinourea derivative of 2,3-diaminopropionic acid. TAN-1057 A and B gradually lost their antibacterial activities in basic aqueous solutions due to hydrolytic opening of the six-membered ring system (Scheme 1). Hydrolysis of TAN-1057 A occurs in both acidic and basic media, and affords the acyclic form (5) with attendant racemization of the α-amino acid stereogenic center. It was also reported that the acyclic form of the molecule can be converted back into the cyclic form via the methyl ester intermediate resulting in a diastereomer mixture (1:1) of TAN-1057A and B.

Scheme 1

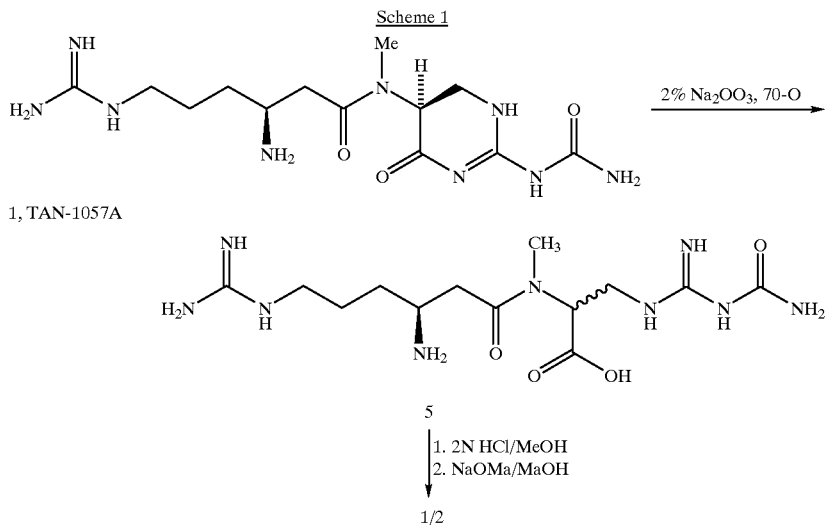

Both TAN-1057C and TAN-1057D have a 7-membered heterocyclic ring; however, they are labile substances that were reported to rapidly convert to a mixture of TAN-1057A/B upon standing in water.

There are the only a few compounds that to date are known to be effective antibiotics against infections caused by MRSA. Furthermore, to date, no one heretofore has synthesized any of the TAN-1057A-D compounds; they have only been isolated from the Flexibacter strain in the soil.

The present inventors, however, have not only found other drugs that are useful antibiotics against bacterial infections, including those caused by MRSA, but also have developed synthetic methods for preparing these compounds, including TAN-1057A-D.

SUMMARY OF THE INVENTION

The present invention is directed to antibiotics of the formula:

I

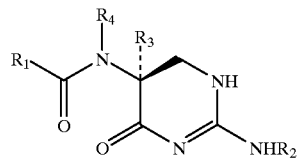

or pharmaceutically acceptable salts thereof, wherein

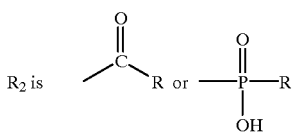

or pharmaceutically acceptable salts thereof;

R is hydrogen, lower alkyl, aryl, lower arylalkyl, lower alkoxy, lower arylalkoxy or aryloxy;

$R_3$ and $R_4$ are independently hydrogen or lower alkyl;

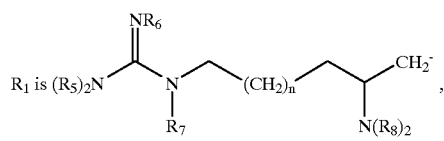

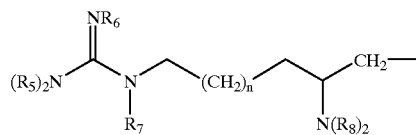

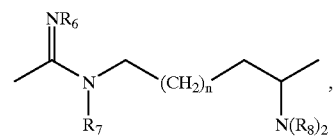

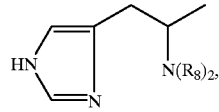

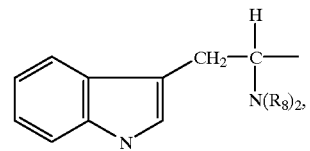

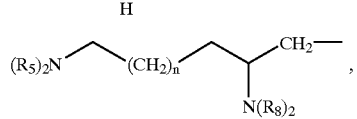

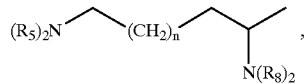

-continued

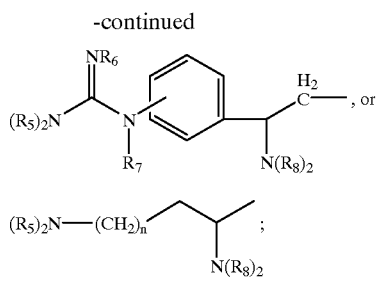

each $R_5$ is the same or different and is hydrogen or lower alkyl;

each $R_8$ is the same or different and is hydrogen or lower alkyl;

$R_6$ and $R_7$ are independently hydrogen or loweralkyl; and n is 1–5.

The present application is also directed to pharmaceutical compositions comprising a pharmaceutically effective amount of the compound of Formula I in association with a pharmaceutical carrier.

In another embodiment, the present invention is directed to a method of treating an animal with a malady caused by bacterial infections which comprises administering to said animal an antibiotically effective amount of a compound of Formula I. In a preferred embodiment, the present invention is directed to the use of the compounds of the present invention in treating an animal afflicted with a disease caused by MRSA. The present compounds are useful antitumor agents and another aspect of the present invention is directed to a method for inhibiting the growth of tumor cells in an animal which comprises administering to said animal an anti-tumor effective amount of a compound of Formula I.

Another aspect of the present invention is directed to a method of preparing compounds of Formula I which comprises (a) reacting a protected amino acid of the formula

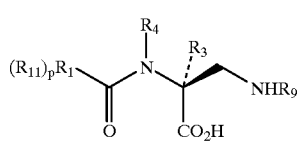

with a compound of the formula

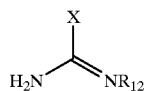

in the presence of a coupling agent under effective coupling conditions to form a product of the formula:

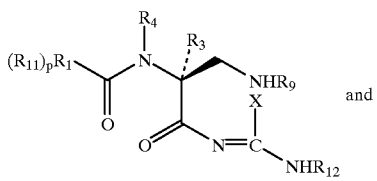

(b) reacting the product of step (a) under conditions effective to remove the protecting group $R_9$ and then reacting the product thereof with an effective amount of base to effect intramolecular cyclization and form the cyclic amidinourea of formula I.

In this process $R_9$ is an amino protecting group;

X is $S-R_{10}$, S-heter $OR_{10}$, halide, $SO_2R_{10}$, or a nitrogen containing heteroaromatic, containing 5 to 10 ring atoms and 1, 2 or 3 nitrogen ring atoms, $R_{10}$ is lower alkyl, aryl, or loweraryllalkyl, $R_{11}$ is a different amino protecting group than $R_9$, substituted on $R_1$, $R_{12}$ is $R_2$ or an amino protecting group different from $R_9$, heter is a nitrogen containing heteroaromatic containing 6 or 10 ring atoms, the heteroaromatic ring contains 1, 2 or 3 heteroatoms, and the ring heteroatoms are nitrogen;

p is 0–3, and $R_1$, $R_2$, $R_3$, $R_4$, $R_5$, $R_6$, $R_7$, $R_8$ and n are as defined hereinabove.

In another aspect, the present invention is directed to the process of preparing TAN-1057C-D. Another aspect of the present invention is directed to the intermediates of these processes.

DETAILED DESCRIPTION OF THE PRESENT INVENTION

As used herein, the term "lower alkyl" is an alkyl group containing 1–6 carbon atoms. The alkyl group may be straight chained or branched. Examples include methyl, ethyl, n-propyl, isopropyl, n-butyl, sec-butyl, isobutyl, t-butyl, n-pentyl, amyl, n-hexyl, and the like. Preferred alkyl groups contain 1–3 carbon atoms, and especially are methyl.

The term "aryl", as used herein, refers to an aromatic ring containing 6–14 ring carbon atoms. The aryl group may be unsubstituted or substituted with additional alkyl groups, so that the total number of carbon atoms present in aryl ranges from 6 to 20 carbon atoms. Examples include phenyl, α-naphthyl, β-naphthyl, tolyl, xylyl, and the like. The preferred aryl group is phenyl.

Arylalkyl refers to an alkyl group, as defined herein, bridging the main chain and an aryl group, as defined herein. Examples include benzyl, phenethyl and the like.

The terms "lower alkoxy," "aryloxy" and "lower arylalkoxy" refer to an O-alkyl group, O-aryl group, O-arylalkyl group, respectively, wherein the alkyl, aryl or arylalkyl group are bridged to the main chain through an oxygen atom.

The term "coupling agent" refers to a "peptide coupling agent" that is used to form amide bonds in peptide synthesis. These are reagents that are known to the skilled artisan.

Examples include carbodiimide, e.g., DCC, 1-(3-dimethyl-amino propyl)-3-ethyl carbodiimide (EDCI) and salts thereof, and the like.

"Protecting group" as used herein refers to an amino protecting group. Such groups are also known to the skilled artisan. Examples of amino protecting groups are found in "Protecting Groups in Organic Synthesis," by T. W. Greene, John Wiley & Sons, pp. 218–287 (1981), the contents of which are incorporated by reference.

The "nitrogen containing heteroaromatic" as used herein refers to a 5 to 10 membered mono or bicyclic heteroaromatic containing 5, 6 and up to 10 ring atoms and at least 1 ring nitrogen atom. The heteroaromatic ring preferably contains up to 3 ring heteroatoms and the remainding ring atoms are carbon atoms. It is preferred that all of the ring heteroatoms in the heteroaromatic are nitrogen. If the heterocycle contains a ring having 5 ring atoms, it is preferred that bonding to the ring is through a nitrogen ring atom. On the other hand, if the heteroaromatic contains a ring having 6 ring atoms, it is preferred that the heteroaromatic ring is substituted with a sulfur atom, which acts as a bridge between the heteroaromatic and the main chain. In this embodiment, it is preferred that the sulfur atom is connected to the heteroaromatic by a bond to a ring carbon atom. Examples of nitrogen containing heteroaromatics include pyrazole, 1, 2, 3-triazole, 1, 2, 4-triazole, 2, 3, or 4-thiopyridine, 2, 3, 4 or 6 thiopyrimidine, 2, 3, 5, or 6-thiopyrazine or a thiotriazine. Preferred heteroaromatics include

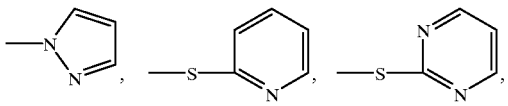

and the like. The present invention is directed to compounds of Formula I wherein n and $R_1$–$R_8$ are as defined hereinabove.

A preferred value of $R_2$ is

It is preferred that R is loweralkyl, especially alkyl containing 1–3 carbon atoms and most preferably methyl. Another preferred value of R is lower alkoxy, especially alkoxy containing 1–3 carbon atoms, and most especially methoxy.

It is preferred that $R_3$ and $R_4$ are independently hydrogen or lower alkyl. The most preferred alkyl is an alkyl containing 1–3 carbon atoms, and especially methyl. It is most preferred that $R_4$ is methyl and $R_3$ is hydrogen.

It is preferred that each $R_5$ is independently hydrogen or alkyl containing 1–3 carbon atoms. The most preferred alkyl is methyl. The most preferred value of $R_5$ is hydrogen. It is even more preferred that each $R_5$ is the same and that each one is alkyl containing 1–3 carbon atoms, and most especially hydrogen.

It is preferred that each $R_8$ is independently hydrogen or alkyl containing 1–3 carbon atoms. The most preferred alkyl is methyl. The most preferred value of $R_8$ is hydrogen. It is even more preferred that each $R_8$ is the same. It is most preferred that each $R_8$ is the same and that each one is alkyl containing 1–3 carbon atoms, and most especially hydrogen.

When $R_7$ and the $R_6$ are present, it is most preferred that they are independently alkyl containing 1–3 carbon atoms and especially hydrogen.

It is most preferred that $R_5$, $R_6$, $R_7$, and $R_8$ are all the same and are alkyl containing 1–3 carbon atoms (e.g., methyl) and most especially hydrogen.

The most preferred value of $R_1$ is

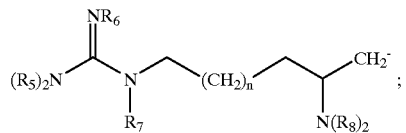

wherein n, $R_5$, $R_6$, $R_7$ and $R_8$ are as defined hereinabove. In this embodiment, it is most preferred that $R_5$, $R_6$, $R_7$ and $R_8$ are independently alkyl containing 1–3 carbon atoms or hydrogen. It is more preferred that $R_5$, $R_6$, $R_7$ and $R_8$ are the same and it is most especially preferred that $R_5$, $R_6$, $R_7$ and $R_8$ are all hydrogen.

The compounds of the present invention are synthesized via the scheme described hereinabove.

In the first step of the scheme, a compound of Formula 1 is reacted with a compound of Formula 2 under amide forming conditions in the presence of a coupling agent to form a product of Formula 3. It is preferred that X is $SR_{10}$, wherein $R_{10}$ is as defined hereinabove. As the coupling agent, a carbodiimide is preferred. It is noted that the amino group in the compound of Formula 1 has an amino protecting group thereon. As indicated hereinabove, various amino protecting groups known in the art can be utilized, such as for example, BOC (t-butyloxycarbonyl) or CBZ (carbobenzyloxy). The group $R_{11}$ is an amino protecting group which is substituted on the free amino group, if any, on $R_1$. The group $R_{11}$ may or may not be present on $R_1$. If it is not present on $R_1$, then p is 0. If it is present on $R_1$, then p has a value greater than 0, i.e., 1, 2 or 3. The protecting group $R_{11}$ is utilized when there is a free amino group on $R_1$. Although each $R_{11}$ may be the same or different, it is preferred that all $R_{11}$ groups are the same. However, if present, $R_{11}$ is different from $R_9$ so that $R_9$ can be sequentially removed without removal of $R_{11}$ as illustrated hereinbelow.

$R_{12}$ is either $R_2$ or any amino protecting group. If $R_2$ is other than an amino protecting group, then $R_{12}$ is $R_2$. However, if $R_2$ is an amino protecting group, then $R_{12}$ is different than $R_9$ and remains in tact under conditions in which $R_9$ is removed. It is preferred that if $R_{12}$ is an amino protecting group, then $R_{12}$ is the same as $R_{11}$. A preferred group for $R_{12}$ when it is an amino protecting group is CBZ.

Removal of the protecting group $R_9$ followed by treatment with an effective amount of base will afford the cyclic amidinourea of Formula I. The present inventors found, however, that the conditions for this latter reaction are critical. A weak base and preferably an organic base, and more preferably a hydrocarbyl (containing only carbon and hydrogen atoms) amine, should be utilized. A triloweralkyl amine is preferred, i.e., a compound of Formula $R_{21}R_{22}R_{23}N$ wherein $R_{21}$, $R_{22}$, and $R_{23}$ are the same or different and are lower alkyl or hydrogen. It is preferred that $R_{21}$, $R_{22}$, and $R_{23}$ are the same and are all alkyl. Moreover, it is preferred that the amine is a tertiary amine, such as $Et_3N$. In addition, even when the reaction is conducted in the presence of a weak base, by-products, such as a bicyclic structure, may be formed especially if excessive amount of base is utilized. Therefore, to minimize the amount of by-product formed, the amount of base utilized should be an effective amount to effect coupling. Preferably, the amount used should range from about ½ mole to about 2 moles per mole of Compound 1. In addition, the reaction should be conducted at a time sufficient to effectuate coupling and minimize by-product formation.

If any of the other groups, $R_1$, or $R_3$–$R_8$ are sensitive to the reaction conditions, these groups also should be protected by protecting groups known in the art. Examples of these various protecting groups are well known in the art and are described in "Protecting Groups in Organic Synthesis" by T. W. Green, John Wiley & Sons (1981), the contents of which are incorporated by reference.

An exemplary procedure of the present process is depicted in Scheme 2.

of $R_{11}$. For example, if the $R_{11}$ group is CBZ, hydrogenation will remove the CBZ group, thereby producing the compound of Formula I.

In these reactions described hereinabove, the reactions are preferably conducted in an inert organic solvent. The preferred solvent is methylene chloride, ethers, such as diethyl ether, THF, dioxane and the like. The reactions are effected at effective temperatures. The preferred temperature is at about room temperature, although the reactions may be conducted at temperature ranging from about 5° C. to the reflux temperature of the solvent.

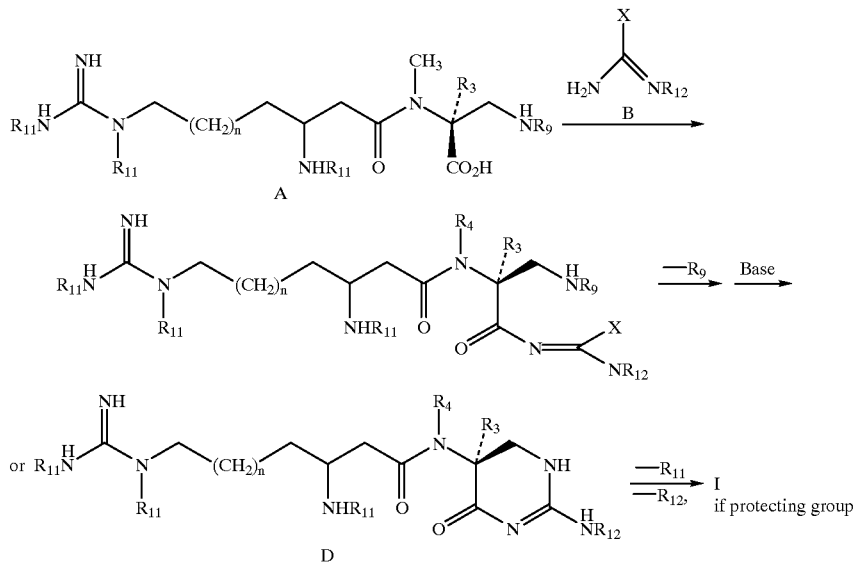

wherein R, $R_1$–$R_{10}$ and n are as defined hereinabove and $R_{11}$ is an amino protecting group which is different from $R_9$.

In the first step of the reaction, the compound of Formula A is reacted with a compound of Formula B in the presence of an effective amount of a coupling agent, as described hereinabove, to form a product of Formula C. To promote the intramolecular reaction, it is critical to have two different protecting groups on the right side and the left side of the molecule which are differentially protected and subsequently unmasked. For example, one protecting group, such as that of $R_9$ may be sensitive to acid, while the other protecting group, $R_{11}$ is inert to acid; it is removed under different conditions. Thus, treatment with acid removes one of the protecting groups but leaves the other protecting group intact. For example, if the protecting groups $R_{11}$ is CBZ and $R_9$ is BOC, acid will remove the $R_9$ protecting group while leaving the other protecting group intact.

The next step is the reaction of the deprotected product with an effective amount of base under conditions effective for intramolecular cyclization as described hereinabove.

Removal of the other protecting group $R_{11}$ will produce the compound of Formula I. The protecting group $R_{11}$ is removed by techniques known to the skilled artisan. Of course, the procedure utilized is dependent upon the identity In planning the synthetic routes, the inventors found that the choice of the protecting groups was viewed as being critical to an ultimately successful approach. In addition, the unusual and labile cyclic amidinourea was targeted to be constructed in the late stages of the synthesis. It was deemed crucial to orchestrate the selective assembly of blocking groups such that: (1) the guanidine group of the homoarginine moiety or other $R_1$ group could be kept inert, (2) the amino group at C-5 could be methylated selectively, and (3) the 1-amino and the free amino groups on $R_1$, if any, could be differentially protected and sequentially unmasked.

The compound of Formula A (in Scheme 2) is prepared using synthetic techniques known in the art. An exemplary procedure is as follows and is illustrated using CBZ-L-arginine and phthalimido protected 2,3-diamino propionic acid. Commercially available tri-N-Cbz-L-arginine (6) is preferred as the core starting material since catalytic hydrogenation is compatible with the final unmasking of the fully derivatized, protected structure. The phthalimido group was preferably chosen to block N1 since this group permits the selective N-methylation and is removed under relatively mild conditions.

Tri-N-Cbz-β-homoarginine (7) was prepared through a modified Arndt-Eistert synthesis with a 1:1 mixture of t-butyl alcohol and water as solvent. This permitted the preparation of the free acid without a saponification step. (Scheme 3).

Scheme 3

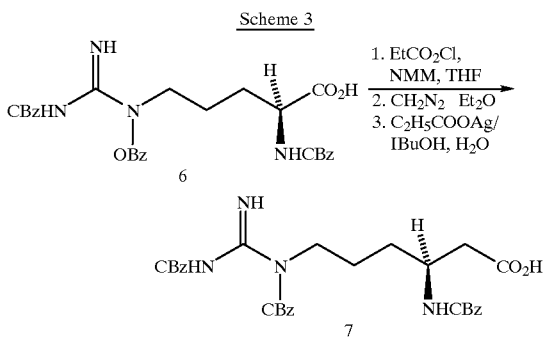

Next, the 2,3-diaminopropionic acid subunit was prepared.

(2S)-N²-Cbz-N²-methyl-N³-phthalimido-2,3-diaminopropionic acid (8) was prepared using L-N-CBZ-asparagine as starting material, according to the literature procedure described in Waki, et al. in *Synthesis* 1981, 260, the contents of which are incorporated by reference. Employing concentrated sulfuric acid and isobutene, 8 was converted to 9. Reductive removal of the N-CBZ group provided the amino compound 10 (Scheme 4).

Scheme 4

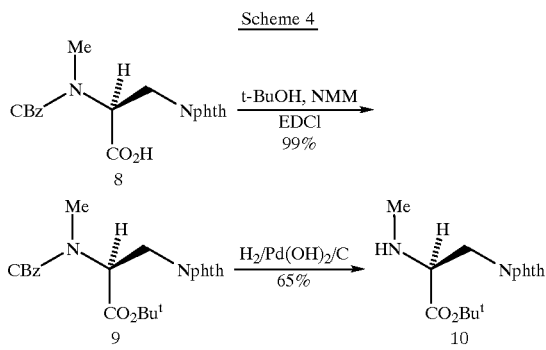

As indicated hereinabove, a critical step in developing a general synthetic approach to this new class of peptide antibiotics relied heavily on an efficient preparation of the cyclic amidinourea moiety. Although the synthesis of this heterocycle has not heretofore been described, acyclic amidinoureas have been previously described in the literature, but the methodology used heretofore is unsatisfactory. All of the published methods, which include the reaction of guanidines with isocyanates, hydrogenation of 5-amino-3-amino-1,2,4-oxadizoles, or the hydrolysis of cyanoguanidines under strongly acidic conditions are either, inefficient, involve harsh reaction conditions, or require numerous steps. The inventors have found that none of these methods were suitable for accessing the labile TAN-1057 amidinourea substructure. Instead, they prepared it by using a compound of the formula

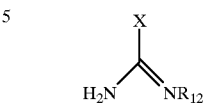

as defined hereinabove. It is preferred that an urea derivative is utilized, as descried hereinabove and in accordance with the synthetic route outlined in Scheme 5. In preparing the TAN-1057A-B derivatives, it is preferred that the compounds are prepared using N-(benzyloxycarbonyl)ureido-N'-benzyloxycarbonyl-S-methylisothiourea (13) under very mild conditions. N-(benzyloxycarbonyl)ureido-N'-benzyloxycarbonyl-S-methylisothiourea (13) was prepared using techniques known in the art, such as by treatment of N-benzyloxycarbonylureido-N'-butoxycarbonyl-S-methylisothiourea with trifluoromethylacetic acid (TFA). The N-benzyloxycarbonylureido-N'-butoxycarbonyl-S-methylisothiourea was prepared from reacting mono-t-butoxycarbonyl-S-methylthiourea with benzyloxycarbonyl-isocyanate (THF, 100%). The mono-t-butoxycarbonyl-S-methylisothiourea was readily obtained by the slow addition of one equivalent of a solution of di-tert-butyldicarbonate in $CH_2Cl_2$ to a cold mixture of S-methylisothiourea semisulfate in $CH_2Cl_2$/2N NaOH. The bis-acylated product, N,N'-bis(benzyloxycarbonyl)-S-methylisothiourea was also produced, but was easily separated by silica gel column chromatography.

Utilizing 13 and 10, the preparation of TAN-1057A compounds are specifically illustrated in Scheme 5, in accordance with the process described hereinabove.

Coupling of tri-N-Cbz-homoarginine (7) and 10 with BOP-Cl provides the desired peptide 25 in good yield. Using methylamine in ethanol followed by treatment with TFA gave the corresponding N-methylamide (26). When peptide 25 was treated with 30% methylamine in EtOH for more than five minutes, one of the N-CbZ groups was removed. However, if the reaction was stopped after 5 min, the partially deprotected derivative is obtained without concomitant loss of the N-CbZ groups. Thus, the reaction of a weak base with the peptide is conducted for a time sufficiently long to permit amide formation and sufficiently short to prevent loss of a protecting group. This can be determined by the skilled artisan without an undue amount of experimentation. The mono-acylated amino was next converted to the corresponding BOC-protected amine 27 by treatment with excess triethylamine in the presence of BOC-ON in dioxane/water.

Scheme 5

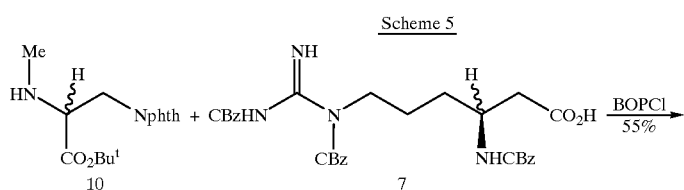

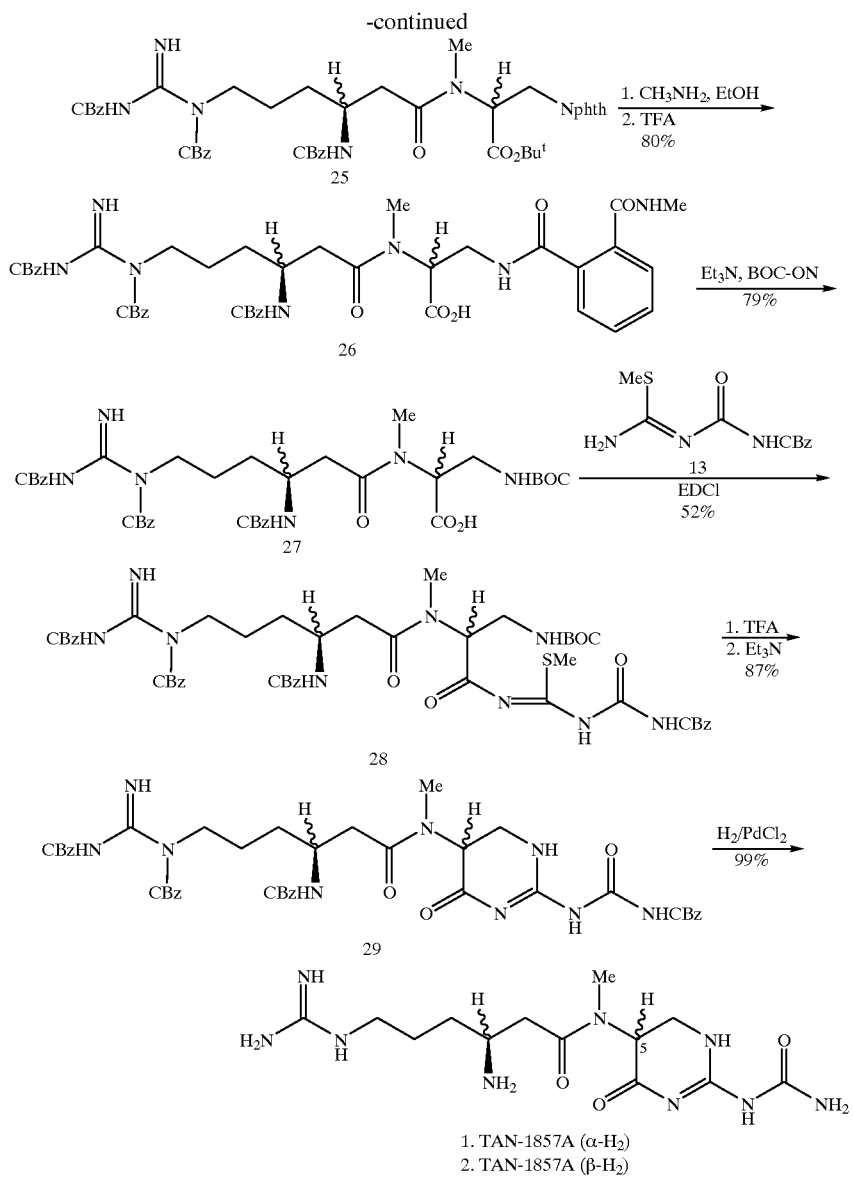

Compound 27 was coupled to N-(benzyloxycarbonyl)ureido-S-methylisothiourea 13 to give 28 in moderate yield. Deprotection of the N-t-BOC group with TFA produced the corresponding TFA salt. When this substance was treated with triethylamine (2.0 eq.), cyclization ensued to furnish the desired, fully protected TAN-1057A derivative 29. This substance proved to be labile undergoing a second cyclization to form a bicyclic by-product. Fortunately, this problem was circumvented by converting 29 into TAN-1057A immediately after PTLC purification. The deprotection was very efficient with hydrogen (60 psi) and $PdCl_2$ in methanol for 24 hours. Pure TAN-1057A was obtained after simple work-up.

Another variation is described in Schemes 6 and 7. As shown in Scheme 6, dipeptide 27 was prepared as previously described as a 1:1 mixture of stereoisomers at the C-5 stereogenic center. Condensation of 27 with the S-methylisothiourea derivatives 79a~e (Scheme 7) in the presence of EDCI yielded derivatives 71a~e (Table 1). Treatment of 71a~e with TFA removed the BOC protecting group and the incipient amine was cyclized with triethylamine to furnish the cyclic amidinourea derivatives 72a~e. Finally, removal of the three N-CBZ groups was effected in high yield by catalytic hydrogenation yielding the TAN-1057 analogs 73a~e.

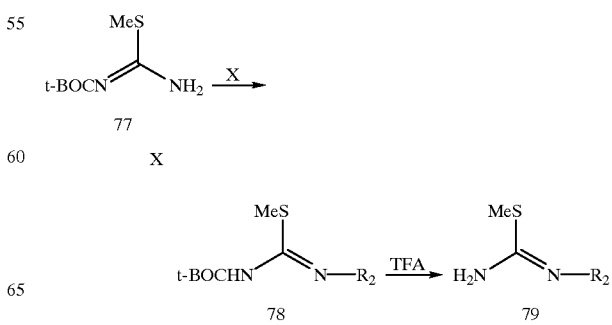

| X | Product |
|---|---|
| a, (CH₃CO)₂ | 78a, R₂ = Ac |
| b, PhCOCl | 78b, R₂ = COPh |
| c, CH₃OCOCl | 78c, R₂ = OCOMe |
| d, CH₃SO₂Cl | 78d, R₂ = SO₂Me |
|  | 78e, R₂ = CBz | wherein

X is an acylating derivative of

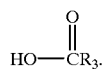

The % yields for each of the steps are indicated in Table 1.

Tan-1057C and TAN-1057D are also labile substances that were reported to rapidly convert to a mixture of TAN-1057A/B upon standing in water. Utilizing the methodology developed for the synthesis of TAN-1057A/B reported above, the synthesis of these seven-membered ring isomers was undertaken as shown in Scheme 8. L-N$^\alpha$-t-BOC-N$^\delta$, N$^\omega$-di-Cbz-β-homoarginine (31) was prepared from commercially available 30 in the same manner as that used for compound 7. Coupling of 31 with d,1–10 in the presence of BOP-Cl, gave the desired peptide 32. Treatment of 32 with TFA effected removal of the BOC group and t-butyl ester; cyclization was effected with TBTU (10-benzo-triazol-1-yl-N,N,N',N'-tetramethyluronium tetrafluoroborate) furnishing 33. In addition to the desired cyclic peptide, macrocyclic dimer was also isolated in approximately the same molar ratio to that of 33; this substance was easily removed by

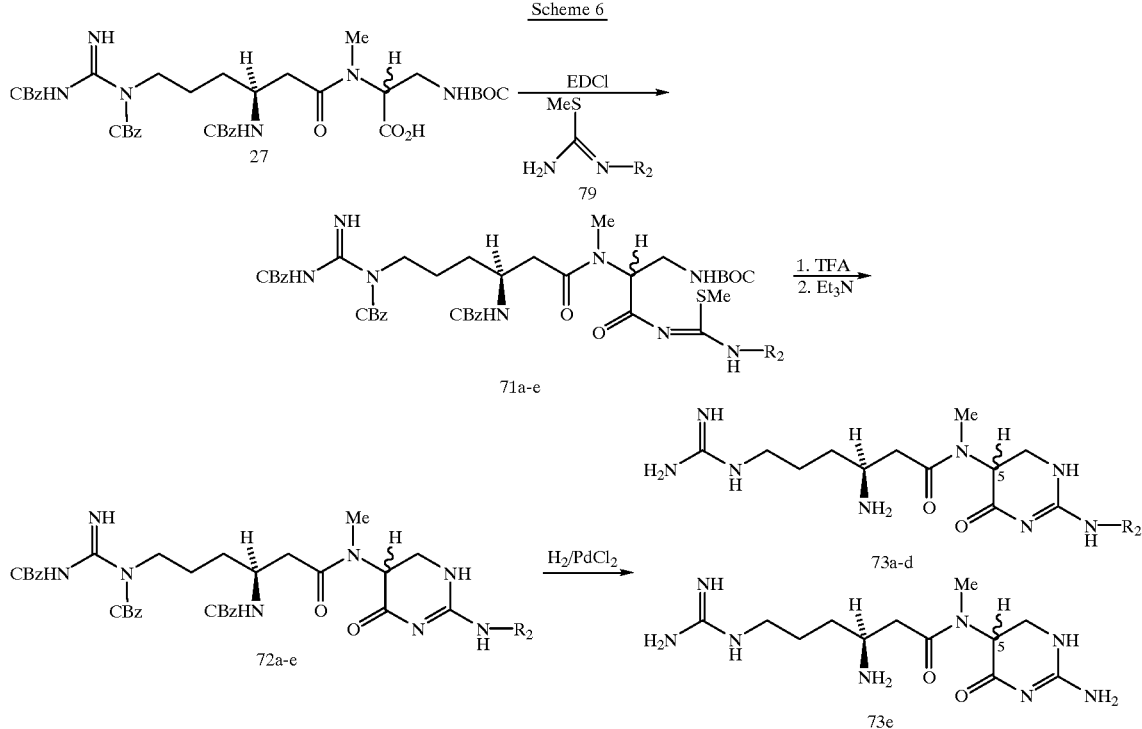

Scheme 6

TABLE 1

Scheme 7

| Entry | R₂ | 71, Yield % | 72, Yield% | 73, Yield% |
|---|---|---|---|---|
| a | Ac | 52 | 32 | 99 |
| b | COPh | 39 | 10 | 99 |
| c | COOMe | 38 | 22 | 89 |
| d | SO₈Me | 34 | 58 | 99 |
| e | CO₈CH₂Ph | 52 | 50 | 99 | preparative thin layer chromatography. Dilution of the reaction mixture of the peptide coupling did not, unfortunately, significantly diminish the amount of dimer formed.

Cleavage of the phthaloyl group by the sequential addition of methylamine caused ring-opening, and addition of BOC-ON gave 34. Treatment of this substance with TFA followed by guanidylation with reagent 35 gave the desired, fully protected product 36 accompanied by the unexpected substance 37. These compounds were separated by chromatography and sequential deprotection of 36 with TFA followed by catalytic hydrogenation gave TAN-1057C (3) and TAN-1057D (4) as an inseparable mixture.

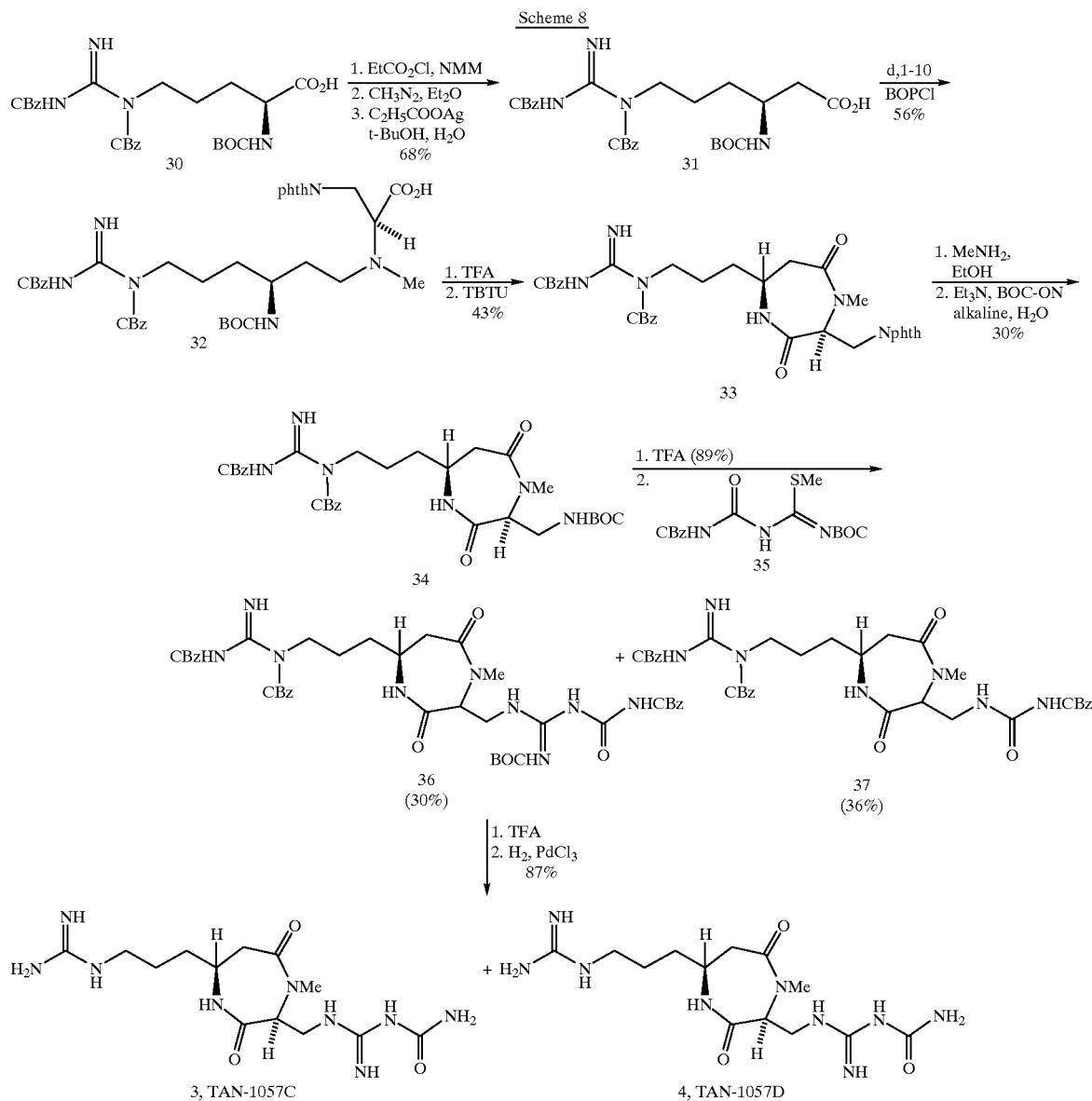
Using the above reaction sequence outlined hereinabove, compounds 124 and 130 are prepared, as outlined in Schemes 9 and 10.
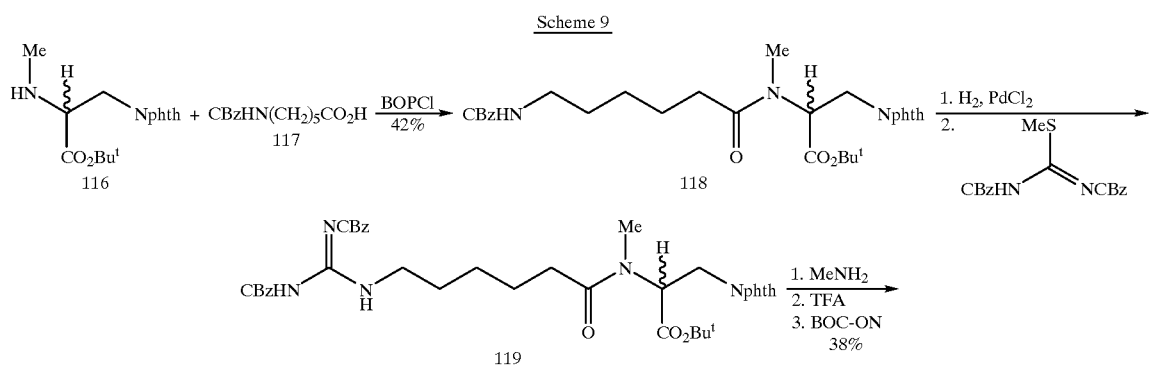

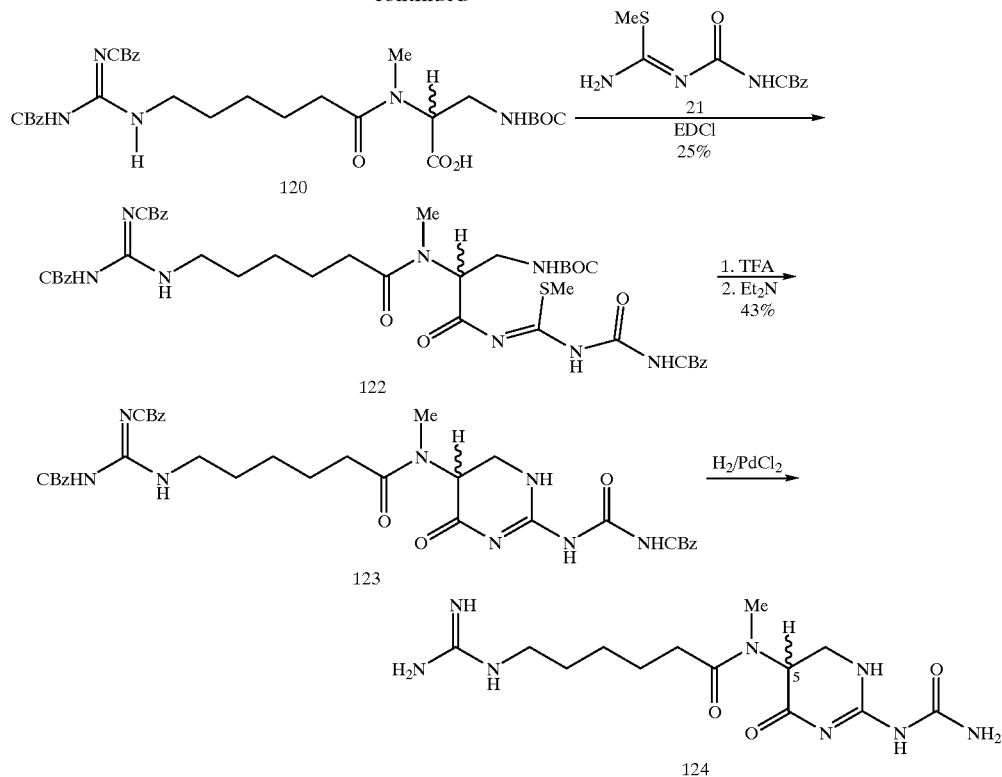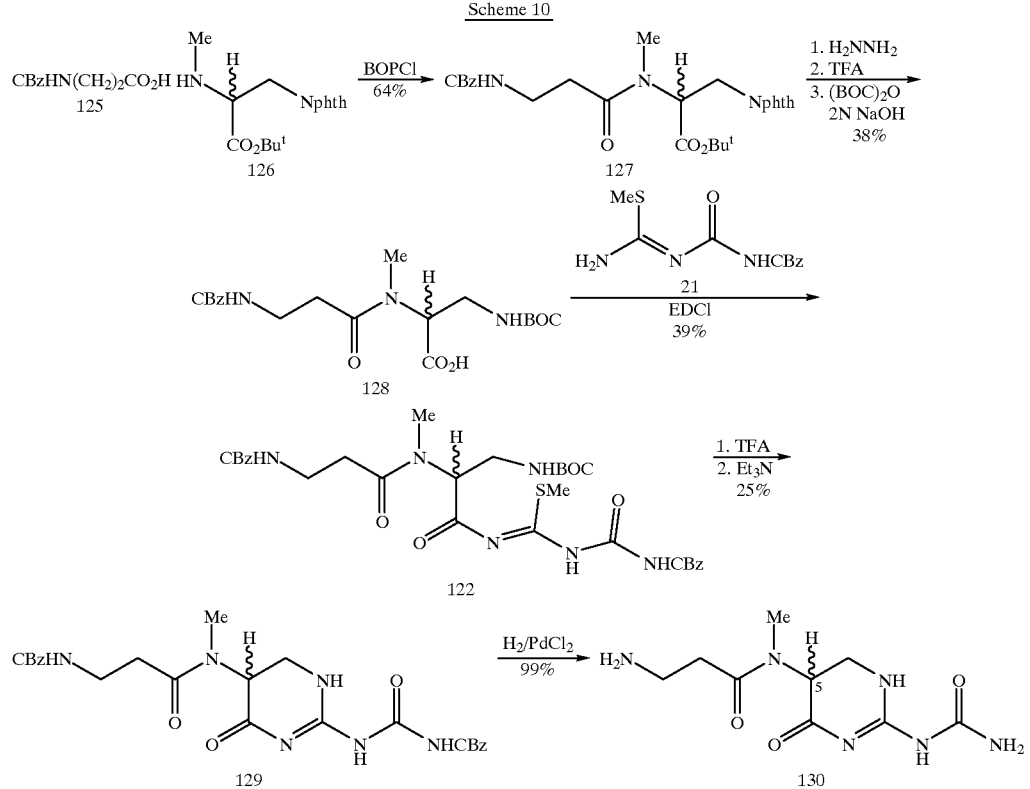

The compounds of the present invention may also be prepared by modifications of the schemes described hereinabove. For example, two or more steps in the synthetic route outlined in Schemes 2–10 may be combined without isolating the product(s) therefrom.

The present new compounds of the present invention form salts when a basic amino function is present. Pharmaceutically acceptable salts are contemplated to be within the scope of the present invention. Basic salts for pharmaceutical use are metal salts including Group I and Group II metals and $NH_4^+$, such as Na, K. Ca, and Mg salts. In addition, acid addition salts, especially hydrochloride or acetate salts, and the like are also useful in pharmaceutical formulations and are encompassed by the present invention.

The compounds of the present invention, including the pharmaceutically acceptable salts thereof, are effective anti-bacterial agents. They display anti-bacterial activity against gram-positive and gram-negative bacteria. They are also effective against various types of drug-resistant bacteria and do not show cross-resistance. In particular, they exhibit significant activity against the MRSA, i.e., methicillin resistant strains, and MSSA, i.e., methicillin sensitive strains. In addition, the compounds of the present invention are also useful anti-tumor agents. They inhibit the growth of malignant tumors, especially solid tumors. Therefore, the compounds of the present invention, including the salts thereof, are useful in the therapeutics of infectious diseases caused by pathogenic microorganisms or tumors in animals, especially mammals, including humans.

The compounds of the present invention can be administered to the host in a variety of forms adapted to the chosen route of administration, i.e., orally, intravenously, intramuscularly or subcutaneously, topically or inhalation butes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, and the like. Such compositions and preparations should contain at least 0.1% of active compound. The percentage of the compositions and preparations may, or course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various anti-bacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally dispersions are prepared by incorporating the various sterilized active ingredient into a sterile vehicle which contains the basic dispersion medium and the required other ingredients form those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The compounds of the present invention may be applied topically, especially when utilized as a bacteriocide. For example, hands, legs, ears, eyes, arms, feet, etc., may be sterilized and disinfected by topical application of the compounds of the present invention. Any common topical formulation, such as a solution suspension, powder, gel, ointment, salve (especially in aerosol form), liquid dispersion and the like, may be used. Preparation of such topical formulations are well described in the art of pharmaceutical formulations, as exemplified, for example, in *Remington's Pharmaceutical Science,* 17th Edition, Mack Publishing Company, Easton, Pa. The compounds of the present invention are present in these topical applications in pharmaceutically effective amounts. The compounds may be present in at least 0.001% by weight of the composition, and preferably from about 0.05% by weight. For example, when used as a liquid, the compounds of the present invention may be dissolved in distilled water at a concentration of about 0.001% to about 0.1% by weight. As an ointment, the pharmaceutical composition may contain approximately 0.01 to 1 mg and, more preferably, 0.02 to 0.5 mg per gram of composition.

Although the compounds shown herein are only drawn with a particular stereoisomer, it is also to be understood the other stereoisomers, including diastereomers and mixtures thereof, including racemic mixtures are effective anti-bacterial agents and are within the scope of the present invention. In particular, these other stereoisomer effective against diseases caused by MRSA.

The following examples further illustrate the invention. These examples are provided solely for illustrative purposes; thus, the present invention should not be limited thereto.

GENERAL

Mass spectra were obtained on a 1992 Fisons VG AutoSpec. HPLC analysis of the compound was carried out using a Waters 6000 pump equipped with a UV detector, utilizing an ODS, YMC Pack A-312 column, using 0.1 M phosphate buffer (pH 5.0) as the mobil phase. All the amino acids used as starting material were purchased from BACHEM Inc. Abbreviations not defined in the text: (BOC)$_2$O=di-tert-butyl dicarbonate; Cbz=carbobenzyloxy; BOC-ON=2-(tert-butoxycarbonyloxyimino)-2-phenylacetonitile; BOP-Cl=Bis (2-oxo-3-oxazolidinyl)phosphinic chloride (Aldrich Chemical Co.); DMAP=4-dimethylamino pyridine (Aldrich Chemical Co.); EDCI=1-(3-dimethylaminopropyl)-3-ethylcarbodiimide hydrochloride (Aldrich Chemical Co.); NMM=4-methylmorpholine (Aldrich Chemical Co.); TBTU=O-benzotrizol-1-yl-N,N,N',N'-tetramethyluronium tetrafluoroborate (Aldrich Chemical Co.); MNNG=1-methyl-3-nitro-1-nitrosoguanidine (Aldrich Chemical Co.).

EXAMPLE 1

L-N$^\alpha$,N$^\delta$,N$^\omega$-tri-CB$_z$-β-homoarginine 7

To a solution of tri-CBz-L-arginine 6 (BACHEM, Inc.) (1.15 g. 2.0 mmol, 1.0 eq)in THF (30 mL) was added NMM (250 μL, 2.2 mmol, 1.1 eq) and ethyl chloroformate (200 μL, 2.2 mmol, 1.1 eq) at 0° C. The resulting mixture was stirred for 1 h at 0° C. The precipitated amino hydrochloride was rapidly filtered off cold. To this clear solution was added CH$_2$N$_2$/ether solution (generated from MNNG) at 0° C. The solution was stirred overnight at room temperature and concentrated to give an oily diazoketone. The diazoketone was dissolved in t-BuOH/H$_2$O (20 mL, 1:1), and to this solution was added silver benzoate (250 mg, 1 mmol, 0.5 eq) and triethyl amine (1 mL). The resulting mixture was stirred overnight in the dark at room temperature and then concentrated in vacuo. The residue was treated with CH$_2$Cl$_2$/sat. NaH$_2$PO$_4$. The organic layer was separated, dried over anhydrous sodium sulfate and concentrated. Purification via column chromatography (silica gel, CH$_2$Cl$_2$:EtOAc:MeOH, 4:4:0.5) provided 717 mg (58%) of 7 as a semi-solid. $^1$H NMR (300 MHz, CD$_3$OD): δ1.47(2H, m); 1.62 (2H, m); 2.40 (2H, d, J=3.84 Hz); 3.91 (3H, m); 5.01 (2H, s); 5.13 (2H, s); 5.23 (2H, s); 7.32 (15H, m) ppm. IR (NaCl, film): 3380, 2954, 1676, 1544, 1451, 1204, 1144, 848, 798 cm$^{-1}$; [α]D$^{25}$=−2.5 (c 1.1, CH$_2$Cl$_2$/CH$_3$OH); Anal. Calcd. for C$_{31}$H$_{34}$N$_4$O$_8$.H$_2$O; C, 61.18; H, 5.96; N, 9.21 Found: C, 61.34; H, 5.83; N, 9.16.

EXAMPLE 2 t-Butyl S-N$^2$-CBz-N$^2$-methyl-N$^3$-Pht-2,3-diminopropionate 9

Cmpd 8 was prepared in accordance with the procedure described in Waki, et al. in *Synthesis* 1981, 261.

To a solution of 8 (3.3 g, 8.64 mmol, 1.0 eq) in CH$_2$Cl$_2$ (200 mL) in a pressure vessel was added H$_2$SO$_4$ (0.4 mL) at −5° C. Isobutene (10 g) was passed into the solution and the vessel was sealed. The resulting mixture was stirred for about 60 h at room temperature. After releasing the pressure, the organic solution was washed with water, 5% NaHCO$_3$ and water. The organic layer was dried over anhydrous MgSO$_4$, filtered and concentrated. Purification via column chromatography (silica gel, CH$_2$Cl$_2$; EtOAc: MeOH, 5:1:0.2) provided 2.84 g (73%) of 9 as a colorless oil. $^1$H NMR (300 MHz, CDCl$_3$ vs TMS): δ1.41/1.47 (9H, S), 2.91 (3H, s), 4.13 (2H, m), 4.97 (2H, m), 5.11 (1H, dd, J=5.46 Hz, J=5.43 Hz), 7.26 (5H, m), 7.71 (2H, m), 7.78 (2H, m) ppm; IR (NaCl, film): 2978, 1774, 1718, 1394, 1306, 1149, 1000, 732 cm$^{-1}$; [α]D$^{25}$=77.7 (c 1.0, CH$_2$Cl$_2$). Anal, Calcd. for C$_{24}$H$_{26}$N$_2$O$_6$: C, 65.74; H, 5.98; N, 6.39. Found: C, 65.52; H, 5.72; N, 6.35.

EXAMPLE 3 t-Butyl N$^2$-methyl-N$^3$-Pht-2,3-diaminopropionate 10

The mixture of 9 (1.30 g, 2.97 mmol) and 10% Pd on carbon (430 mg) in THF (90 mL) was degassed for 10 min with N$_2$. The reaction vessel was then charged with H$_2$ and the mixture was hydrogenated at 18 psi for 48 h. The mixture was purged with nitrogen and filtered to remove the catalyst. The filtrate was concentrated and dried in vacuo to give 780 mg (87%) of 10 as a semi-solid. The crude product can be carried on without further purification. An analytically pure sample was obtained from column chromatography [silica gel, methylene chloride:EtOAc:MeOH, 5:1:0.1]. However, chromatography on silica gel caused racemization. $^1$H NMR (300 MHz, CDCl$_3$ vs TMS): δ1.39 (9H, s), 1.63 (1H, br, D$_2$O exchanged), 2.37 (3H, s), 3.52 (1H, t, J=7.59 Hz), 3.86 (2H, d, J=7.47 Hz), 7.28 (2H, m), 7.85 (2H, m) ppm. IR (NaCl, film): 3388, 2929, 1778, 1750, 1718, 1631, 1503, 1376, 1062 cm$^{-1}$; mp 132° C. (decomp.); [α]D$^{25}$=−18.3 (c 0.76, CH$_2$Cl$_2$, crude product). Anal. Calcd. for C$_{16}$H$_{20}$N$_2$O$_4$: C, 63.14; H, 6.62; N, 9.20. Found: C, 63.30; H, 6.49; N, 9.32.

EXAMPLE 4

L-N$^\alpha$,N$^\delta$,-N$^\omega$-tri-CBz-β-homoarginine methyl ester

To a solution of tri-N-CBz-L-arginine (BACHEM, Inc.) (1.15 g, 2.0 mmol, 1.0 eq) in EtOAc (30 mL) was added NMM (250 μL) and ethyl chloroformate (200 μL) at 0° C. The resulting mixture was stirred for 3 h at 0° C. The precipitated amine hydrochloride was rapidly filtered off in the cold. To this clear solution was added CH$_2$N$_2$/ether solution (generated from MNNG). The solution was stirred overnight at room temperature and concentrated to give an oily diazoketone. The diazoketone was dissolved in MeOH (30 mL), and to this solution was added silver benzoate (250 mg, 1 mmol, 0.5 eq) and triethyl amine (1 mL). The resulting mixture was stirred overnight in the dark at room temperature and then concentrated in vacuo. The residue was dissolved in ethyl acetate and insoluble material was filtered off. The filtrate was washed with saturated sodium bicarbonate solution, saturated sodium chloride solution, 1M hydrochloric acid, and then finally saturated sodium chloride solution. The organic layer was dried over anhydrous sodium sulfate, filtered and concentrated. Purification via column chromatography (silica gel, 5:4:0.2 methylene chloride: EtOAc: MeOH) yielded 873 mg (74%) of L-N$^\alpha$,N$^\delta$-N$^\omega$-tri-CBz-1-homoarginine methyl ester as a white solid. $^1$H NMR (300 MHz, CDCl$_3$ vs TMS): δ1.49 (2H, m), 1.53

(2H, m), 2.48 (2H, d, J=5.40 Hz), 3.58 (3H, s), 3.93 (1H, m), 5.04 (2H, s), 5.10 (2H, s) 5.19 (2H, s) 5.43 (1H, d, J=7.0 Hz, $D_2O$ exchanged), 7.31 (15H, m), 9.30 (1H, br, $D_2O$ exchanged), 9.46 (1H, br, $D_2O$ exchange) ppm. IR (NaCl, film): 3342, 2936, 1697, 1525, 1455, 1248, 1056, 1024, 667 $cm^{-1}$; mp: 139.5–140.5° C.; $[\alpha]D^{25}$=−1.43 (c 0.7, $CH_2Cl_2$); Anal. Calcd. for $C_{32}H_{36}N_4O_8$: C, 63.57; H, 6.00; N, 9.27. Found: C, 63.71; H, 5.81; N, 9.20.

EXAMPLE 5

Peptide 25

To a mixture of the acid 7 (1.50 g, 2.54 mol, 1.0 eq) and NMM (464 µL, 1.2 mmol, 1.3 eq) in $CH_2Cl_2$ (3 mL) was added BOP-Cl (306 mg, 1.2 mmol, 1.2 eq) at 0° C. After stirring 10 min., the amino d, l-10 (970 mg, 3.19 mmol, 1.26 eq) in $CH_2Cl_2$ (3 mL) was added. The resulting mixture was stirred overnight, diluted with $CH_2Cl_2$ (200 mL), washed with brine, dried over anhydrous $Na_2SO_4$, filtered and concentrated. Purification via column chromatography (silica gel, methylene chloride:EtOAc, 6:2) provided 1.22 g (55%) of 25 as an oil. $^1$H NMR (300 MHz, $CD_3OD$): δ1.20 (2H, m); 1.39 (2H, m); 1.43 (9H, s); 2.21 (1H, m); 2.53 (1H, m); 2.92 (3H, s); 3.72 (3H, m); 4.67 (2H, d, J=7.8 Hz); 4.95 (2H, s); 5.08 (2H, s); 5.20 (2H, s); 5.22 (1H, m); 7.33 (15H, m); 7.64 (2H, m); 7.74 (2H, m);7.74 (2H, m) ppm. IR (NaCl, film): 3389, 2936, 1774, 1716, 1646, 1609, 1505, 1395, 1370, 1251, 1100, 1008, 722 $cm^{-1}$; $[\alpha]D^{25}$=−36.1 (c 0.7, $CH_2Cl_2$; this data is for the optically pure diastereomer obtained with (S)-10); Anal. Calcd. for $C_{47}H_{52}N_6O_{11}$: C, 64.37; H, 5.98; N, 9.58. Found: C, 63.38; H, 6.08; N, 9.60.

EXAMPLE 6

Peptide 26

To a solution of 25 (500 mg. 0.57 mmol, 1.0 eq) in $CH_2Cl_2$ (10 mL) was added 2 N methylamine in MeOH (5.0 mL). The mixture was stirred for 5 min and concentrated. Purification via column chromatography (silica gel, methylene chloride:EtOAc:MeOH, 4:1:0.3) provided 500 mg (97%) of the methylamine adduct as an oil. $^1$H NMR (300 MHz, $CD_3OD$): δ1.43 (9H, s); 1.61 (4H, m); 2.55 (1H, m); 2.64 (1H, m); 2.85 (3H, m); 3.03/3.04 (3H, s); 3.70 (1H, m0); 3.86 (4H, m); 4.94 (3H, m); 5.09 (2H, s); 5.21 (2H, s); 7.37 (19H, m) ppm. IR (NaCl, film): 3383, 3280, 3067, 2935, 1717, 1646, 1507, 1456, 1373, 1252, 1098, 697 $cm^{-1}$. Anal. Calcd. for $C_{48}H_{57}N_7O_{11}$: C, 63.49; H, 6.33; N, 10.80. Found: C, 63.51; H, 6.38; N, 10.81. The crude material obtained above (500 mg, 0.55 mmol, 1.0 eq) was treated with anisole (0.2 mL) and TFA (5.0 mL) at 0° C. The resulting mixture was stirred for 1 h at room temperature, concentrated and triturated in dry ether to give 26 (437 mg, 93%) as an oil. $^1$H NMR (300 MHz, $CD_3OD$): δ1.59 (4H, m); 2.53 (1H, m); 2.80 (1H, m); 2.84 (3H, s); 3.03/3.05 (3H, S); 3.87 (5H, m); 4.94 (3H, m); 5.13 (2H, s); 5.22 (2H, s); 7.34 (19H, m) ppm. IR (NaCl, film): 3396, 3290, 2945, 1717, 1684, 1615, 1540, 1378, 1254, 1099 $cm^{-1}$. Anal. Calcd. for ($c_{44}H_{49}N_7O_{11}$.$3H_2O$): C, 58.33; H, 6.12; N, 10.82. Found: C, 58.22; H, 5.93; N, 10.85.

EXAMPLE 7

Carboxylic Acid 27

To a solution of 26 (437 mg, 0.51 mmol, 1.0 eq) in $H_2O$/dioxane (8 mL, 1:1) and $Et_3N$ (715 µL, 5.1 mmol, 10 eq) was added BOC-ON (376 mg, 1.53 mmol, 3.0 eq). The mixture was stirred overnight and extracted with EtOAc (2×100 mL). The organic phase was dried over anhydrous $Na_2SO_4$, filtered and concentrated. Purification via column chromatography (silica gel, $CH_2Cl_2$:MeOH, 9:1) provided 320 mg (79%) of 27 as a semi-solid. $^1$H NMR (300 MHz, $CD_3OD$): δ1.35 (9H, s); 1.65 (4H, m); 2.50 (2H, m); 2.86 (3H, m); 3.60 (3H, m); 3.95 (3H, m); 5.00 (2H, m); 5.10 (2H, s); 5.24 (2H, s); 7.32 (15H, m) ppm. IR (NaCl, film): 3388, 2927, 1714, 1609, 1513, 1454, 1382, 1253, 1173, 1098, 1006, 697 $cm^{-1}$. HRMS (FAB): Cacld. for ($C_{40}H_{50}N_6O_{11}$+H)=791.3616, Found (M+H)=791.3616.

EXAMPLE 8

S-Methylisothiourea 28

To a solution of 27 (70 mg, 0.066 mmol, 1.0 eq), DMAP (25 mg, 0.13 mmol, 2.0 eq) and EDCI.HCl (21 mg, 0.07 mmol, 1.1 eq) in $CH_2Cl_2$ (0.5 mL) was added 13 (Ex. 18) (45 mg, 0.1 mmol, 1.5 eq). The resulting mixture was stirred overnight at room temperature, diluted with $CH_2Cl_2$, washed with brine, dried over anhydrous $Na_2SO_4$, filtered and concentrated. Purification via column chromatography (silica gel, $CH_2Cl_2$:EtOAc:MeOH, 4:1:0.1) provided 36 mg (52%) of 28 as a semi-solid. $^1$H NMR (300 MHz, $CD_3OD$): δ1.39 (9H, s); 1.64 (4H, m); 2.28 (3H, s); 2.60 (1H, m); 2.75 (1H, m); 3.05 (3H, m); 3.47 (1H, m); 3.69 (1H, m); 3.91 (3H, m); 4.94 (3H, m); 5.08 (2H, s); 5.20 (2H, s); 5.23 (2H, s); 7.31 (20H, m) ppm. IR (NaCl, film): 3388, 2969, 1770, 1713, 1647, 1609, 1499, 1251, 1175, 1099 $cm^{-1}$. Anal. Calcd. for $C_{51}H_{61}N_9O_{13}S$: C, 58.89; H, 5.91; N, 12.12. Found: C, 59.03; H, 6.12; N, 12.19.

EXAMPLE 9

Cyclization product 29

To a mixture of 28 (70 mg, 0.067 mmol, 1.0 eq) and anisole (0.1 mL) was added TFA (1.0 mL). the resulting mixture was stirred for 15 min at room temperature. The TFA was evaporated and coevaporated with $CH_2Cl_2$ to dryness. The resulting residue was dried on vacuo for 2 h and triturated with ethyl ether to give a white solid. This white solid was dissolved in THF (1.5 mL). To this solution was added triethylamine (20 µL, 0.14 mmol, 2.0 eq). After stirring 10 min., the solvent was evaporated and the resulting residue was immediately purified by PTLC (silica gel, $CH_2Cl_2$:EtOAc:MeOH, 4:1:0.5) to give 40 mg (67%) of 29 as a white solid. This product was unstable with a tendency to form a bicycle by-product ($t_{1/2}$ is about 1 day) and was used for the next step immediately. $^1$H NMR (300 MHz, $CD_3Cl$/$D_2O$ vs TMS): δ1.62 (4H, m); 2.45 (2H, m); 2.76/2.78 (3H, s); 3.32 (1H, m); 3.70 (1H, m); 3.93 (4H, m); 5.17 (6H, m); 7.32 (20H, m) ppm. IR (NaCl, film): 3381, 3258, 2934, 1765, 1713, 1646, 1608, 1504, 1452, 1252, 1186, 1096, 1063 $cm^{-1}$. MS (ES+): Calcd. for ($C_{45}H_{49}N_9O_{11}$+H)= 892.4. Found (M+H)=892.4; (M+H−108)=784.3.

EXAMPLE 10

3S,5'S/R-3-amino-6-[(aminoiminomethyl)amino]-N-[2-[(aminocarbonyl)amino]-1,4,5,6-tetrahydro-4-oxo-5-pyrimidinyl)-N-methyl-hexanamide, TAN-1057 A/B To a solution of 29 (40 mg, 0.045 mmol, 1.0 eq) in MeOH (1.5 mL)/$CH_2Cl_2$ (0.5 mL) was added $PdCl_2$ (40 mg). The reaction flask was degassed and charged with $H_2$ (1 atm). The mixture was stirred for 30 min. The mixture was then purged with nitrogen, and filtered to remove the catalyst. The filtrate was concentrated and dried in vacuo to give a 2HCl salt of TAN-1057 A/B (½) (1:1, 20 mg, 100% yield) as an amorphous solid. This product was identical in mobility by HPLC, mnr and antibiotic activity by bioassay to authentic TAN-1057 A/B (Takeda). $^1$HNMR (300 MHz, D$_2$O): δ1.77 (4H, m); 2.85 (1H, dd, J=18, 9.3 Hz); 3.00 (1H, dd, J=18, 4.0 Hz); 3.17 (3H, s); 3.27 (2H, t, J=6.0 Hz); 3.70 (1H, m); 3.99 (2H, m); 5.14 (1H, dd, J=12, 8.5 Hz) ppm; IR (KBr pellet): 3350, 3179, 2955, 1696, 1622, 1395, 1205, 1135 cm$^{-1}$. MS (ES$^+$): Calcd. (C$_{13}$H$_{25}$N$_9$O$_3$+H)=356.2, Found (M+H)=356.4.

EXAMPLE 11

L-Nα-t-BOC-Nδ,Nω-di-CBz-homoarginine 31

To a solution of Na-t-BOC-di-CBz-L-arginine 30 (BACHEM) (2.72 g, 5.0 mmol, 1 eq) in THF (50 mL) was added NMM (604 μL, 5.5 mmol, 1.1 eq) and ethyl chloroformate (524 μL, 5.5 mmol, 1.1 eq) at 0° C. The resulting mixture was stirred for 3 h at 0° C. The precipitated amine hydrochloride was rapidly filtered off cold. To this clear solution was added CH$_2$N$_2$/ether solution (generated from MNNG). The solution was stirred overnight at room temperature and concentrated to give an oily diazoketone. The diazoketone was dissolved in t-BuOH/H$_2$O (60 mL, 1:1), and to this solution was added silver benzoate (1.0 g) and triethyl amine (5 mL). The resulting mixture was stirred overnight in the dark at room temperature and then concentrated in vacuo. The residue was treated with ethyl acetate/sat. NaH$_2$PO$_4$ aqueous solution. The organic layer was separated, dried over anhydrous sodium sulfate and concentrated. Purification via column chromatography (silica gel, CH$_2$Cl$_2$:EtOAc:MeOH, 4:4:0.5) provided 1.80 g (65%) of 31 as a semi-solid. $^1$H NMR (300 MHz, CD$_3$OD): δ1.39 (9H, s); 1.42 (2H, m); 1.63 (2H, m); 2.36 (2H, m); 3.83 (1H, m); 3.93 (2H, t, J=7.2 Hz); 5.12 (2H, s); 5.27 (2H, s); 7.36 (10H, m) ppm. IR (NaCl, film): 3386, 3286, 2975, 1718, 1610, 1508, 1456, 1380, 1253, 1174, 1098, 1006, 738, 698 cm$^{-1}$; [α]D$^{25}$=1.8 (c 2.0, CH$_2$Cl$_2$); Anal. Calcd. for C$_{28}$H$_{36}$N$_4$O$_8$: C, 60.42; H, 6.52; N, 10.07. Found: C, 60.30; H, 6.62; N, 10.06.

EXAMPLE 12

Peptide 32

To the mixture of the acid 31 (1.0 g, 1.79 mmol, 1.0 eq) and NMM (255 μL, 2.33 mmol, 1.3 eq) in CH$_2$Cl$_2$ (2 mL) was added BOP-Cl (593 mg, 2.33 mmol, 1.3 eq) at 0° C. After stirring for 10 min., d,l-10 (708 mg, 2.33 mmol, 1.3 eq) in CH$_2$Cl$_2$ (3 mL) was added. The resulting mixture was stirred overnight, diluted with CH$_2$Cl$_2$ (200 mL), washed with brine, dried over anhydrous Na$_2$SO$_4$, and concentrated. Purification via column chromatography (silica gel, methylene chloride:EtOAc, 8:2) provided 838 mg (56%) of 32 as an oil. $^1$H NMR (300 MHz, CD$_3$OD): δ1.16 (2H, m); 1.35 (9H, s); 1.43 (2H, m); 1.45 (9H, s); 2.10–2.55 (2H, m); 2.87/2.91 (3H, m); 3.72 (3H, m); 4.08 (1H, m); 5.10 (2H, s); 5.17 (2H, m); 5.24 (2H, m); 7.38 (10H, m); 7.67 (2H, m); 7.74 (2H, m) ppm. IR (NaCl, film): 3390, 2974, 1716, 1647, 1507, 1368, 1252, 1169, 1099, 1006, 719, 696 cm$^{-1}$. Anal. Calcd. for C$_{44}$H$_{54}$N$_6$O$_{11}$: C, 62.70; H, 6.46; N, 9.97. Found: C, 62.60; H, 6.31; N, 9.79.

EXAMPLE 13

Cyclic Peptide 33

Compound 32 (179 mg, 0.212 mmol, 1.0 eq) was treated with anisole (0.1 mL) and TFA (2.0 mL) at 0° C. The mixture was stirred for 2 h at room temperature, concentrated and triturated in dry ether to give 140 mg of product as a white solid. This solid was dissolved in CH$_2$Cl$_2$ (350 mL). To this solution was added TBTU (84 mg, 0.26 mmol, 1.5 eq) and DIEA (92 μL, 0.51 mmol, 3.0 eq). The resulting mixture was stirred 48 h, washed with brine, dried over anhydrous Na$_2$SO$_4$, filtered and concentrated. Purification by PTLC (silica gel, CH$_2$Cl$_2$:EtOAc:MeOH, 4:1:0.1) provided 50 mg (43%) of 33 as a semi-solid. $^1$H NMR (300 MHz, CD$_3$OD): δ1.40 (1H, m); 1.55 H, m); 1.68 (2H, m); 2.64 (1H, m); 2.81/2.86 (3H, m); 3.13 (1H, m); 3.59 (1H, m); 3.93 (2H, m); 4.18 (2H, m); 4.45 (1H, m); 5.09/5.11 (2H, s); 7.34 (10H, m); 7.78 (4H, m) ppm. IR (NaCl, film): 3389, 3280, 2948, 1773, 1716, 1659, 1608, 1513, 1394, 1253, 1097, 1006, 910, 724 cm$^{-1}$. HRMS (FAB): Calcd. for (C$_{35}$H$_{36}$N$_6$O$_8$+H)+ 669.2672. Found: (M+H) 669.2690.

EXAMPLE 14 t-BOC Amine 34

To a solution of 33 (100 mg, 0.15 mmol, 1.0 eq) in CH$_2$Cl$_2$ (2.0 mL) was added 2 N methylamine/MeOH (2.0 mL) at 0° C. The mixture was stirred for 10 min at 0° C., concentrated and separated on column chromatography (silica gel, methylene chloride:EtOAc:MeOH, 4:1:0.3) to give 84 mg of an oil. To a mixture of the oil obtained above in H$_2$O/dioxane (1 mL, 1:1) and Et$_1$N (217 μL, 1.5 mmol, 10 eq) was added BOC-ON (106 mg, 0.45 mmol, 3.0 eq). The mixture was stirred overnight at room temperature and extracted with EtOAc (2×100 mL). The organic phase was dried over anhydrous Na$_2$SO$_4$, filtered, concentrated and purified by column chromatography (silica gel, eluted with CH$_2$Cl$_2$:MeOH, 9:1) to give 35 mg (38%) of 34 as a semi-solid. $^1$H NMR (300 MH, CD$_3$OD): δ1.42 (9H, s); 1.47 (2H, m); 1.66 (2H, m); 2.63 (1H, m); 2.85 (½H, m); 2.90/2.93 (3H, s); 3.05 (½H, m); 3.52 (2H, m); 3.72 (1H, m); 3.92 (2H,m); 4.25 (1H, m); 5.11 (2H, s); 5.26/5.27 (2H, s); 7.35 (10H, m) ppm. IR (NaCl, film): 3386, 3289, 2934, 1716, 1652, 1609, 1507, 1456, 1366, 1252, 1175, 1095, 1006, 910, 734, 698 cm$^{-1}$. HRMS (FAB) Calcd. for (C$_{32}$H$_{42}$N$_6$O$_8$+H)=639.3142. Found: (M+H)=639.3157.

EXAMPLE 15

Condensation Product 36 and 37

Compound 34 (33 mg, 0.052 mmol) was treated with anisole (0.1 mL) and TFA (1.0 mL) at 0° C. The mixture was stirred for 1 h at room temperature, concentrated and triturated with dry ether to give 32 mg (99%) of the corresponding amine as an oil. A solution of the crude amine (30 mg, 0.046 mmol, 1.0 eq), triethylamine (20 μL, 0.14 mmol, 3.0 eq) and 35 (37 mg, 0.092 mmol, 2.0 eq) (Ex. 17) in CH$_2$Cl$_2$ (1.0 mL) was stirred 4 h at room temperature. The resulting mixture was poured into EtOAc, washed with brine, dried over anhydrous Na$_2$SO$_4$, filtered, concentrated and separated on PTLC (silica gel, CH$_2$Cl$_2$:EtOAc, 7:3) to give 12 mg (30%) of 36 as a semi-solid and 13 mg (39%) of 37 as an oil. 36: $^1$H NMR (300 MHz, CD$_3$OD): δ1.42 (2H, m); 1.48 (9H, s); 1.67 (2H, m); 2.70 (1H, m); 2.83/2.89 (3H, s); 2.98 (1H, m); 3.62 (2H, m); 3.91 (3H, m); 4.67 (1H, m); 5.10 (2H, s); 5.14 (2H, s); 5.26 (2H, s); 7.35 (15H, m); ppm. IR (NaCl, film): 3384, 3293, 2932, 1716, 1722, 1651, 1491, 1254, 1144, 1008 cm$^{-1}$. HRMS (FAB): Calcd. for (C$_{42}$H$_{51}$N$_9$O$_{11}$+H)=858.3786. Found: (M+H)=858.3763. 37: $^1$H NMR (300 MHZ, CD$_3$OD): δ1.45 (2H, m); 1.67 (2H, m); 2.73 (1H, m); 2.82 (1H, m); 2.85/2.91 (3H, s); 3.54 (1H, m); 3.70 (1H, m); 3.91 (3H, m); 4.44 (1H, t, J=9 Hz); 5.10

(2H, m); 5.14 (2H, m); 5.27 (2H, m); 7.35 (15H, m) ppm. IR (NaCl, film): 3385, 3272, 2931, 1715, 1651, 1494, 1455, 1379, 1241, 1092 cm$^{-1}$. HRMS (FAB): Calcd. for ($C_{36}H_{41}N_7O_9$+H)+716.3044. Found (M+H)=716.3021.

EXAMPLE 16

[[[[5-[3-[(aminoiminomethyl)amino]propyl] hexahydro-(2S/R,5S)-1-methyl-3,7-dioxo-1H-1,4-diazepin-2-yl]methyl]amino]iminomethyl]urea,TAN-1057 C/D (3 and 4)

Compound 36 (10 mg, 0.012 mmol) was treated with anisole (0.1 mL) and TFA (1.0 mL) at 0° C. The mixture was stirred for 1 h at room temperature, concentrated and purified by PTLC (silica gel, $CH_2Cl_2$:MeOH, 6:1) to give 6.0 mg of a semi-solid. To a solution of this substance (6 mg, 0.0066 mmol, 1.0 eq) in MeOH (1.0 mL)/$CH_2Cl_2$ (0.5 mL) was added $PdCl_2$ (8.0 mg). After degassing with $N_2$, the reaction mixture was charged with $H_2$ (1 atm.) and the mixture was hydrogenated for 10 min. The mixture was then purged with nitrogen, and filtered to remove the catalyst. The filtrate was concentrated and dried in vacuo to give a 2HCl salt of TAN-1057 C/D (1:1, 3 mg~100% yield) as an amorphous solid. $^1$H NMR (300 MHz, DMSO-d6 vs TMS): δ1.51 (4H, m); 2.82 (3H, s); 2.70–2.90 (2H, m); 3.09 (2H, m); 3.43 (1H, m); 3.79 (2H, m); 4.66 (½H, m); 4.75 (½H, m); 7.26 (6H, m); 7.86 (1H, br); 8.06 (1H, br); 8.70 (2H, br); 9.15 (1H, br); 10.35 (1H, br) ppm. MS (FAB): Calcd. for ($C_{13}H_{25}N_9O_3$+H)=356.2. Found: (M+H)=356.3; (M+2H)$^{++}$=178.7. Upon standing in 0.1 M phosphate buffer at pH=5, the mixture of 3 and 4 had reverted to a mixture of 1 and 2.

EXAMPLE 17

N-(Benzyloxycarbonyl)ureido-N'-t-butyloxycarbonyl-S-methylisothiourea (35)

To a solution of t-butyloxycarbonyl-S-methylisothiourea (1.69 g, 8.91 mmol, 1.0 eq) in THF (40 mL) was added N-benzyloxycarbonylisocyanate (1.90 g, 10.73 mmol, 1.2 eq). The resulting mixture was stirred for 10 min at room temperature and concentrated. Purification via column chromatography (silica gel, $CH_2Cl_2$:EtOAc:MeOH, 4:4:0.5) provided 3.25 g (100%) of 35 as a white solid. $^1$H NMR (300 MHz, $CDCl_3$ vs TMS): δ1.48 (9H, s); 2.32 (3H, s); 5.22 (2H, s); 7.37 (5H, m); 7.50 (1H, br, $D_2O$ exchange); 11.96 (1H, br, $D_2O$ exchange) ppm. IR (NaCl, film): 3270, 2979, 1747, 1664, 1570, 1476, 1370, 1275, 1207, 1138, 1072, 1056 cm$^{-1}$, mp: 120–3° C.; Anal. Calcd. for $C_{16}H_{21}N_3O_5S$: C, 52.30 H, 5.76 N, 11.44. Found: C, 52.15; H, 5.73 N, 11.38.

EXAMPLE 18

N-(Benzyloxycarbonyl)ureido-S-methylisothiourea (13)

Compound 35 (401 mg, 1.0 mmol) was treated with TFA (1.0 mL) and was stirred for 30 min at room temperature, evaporated to dryness and dried under reduced pressure for 2 h, triturated with anhydrous $Et_2O$ to give 400 mg of 13 as a solid. This crude product was carried on without further purification. $^1$H NMR (300 MHz, $CD_3OD$): δ2.64 (3H, m); 5.21 (2H, m); 7.31 (5H, m) ppm. IR (NaCl, $CH_2Cl_2$): 3252, 2959, 1790, 1682, 1203, 1137, 1025, 778, 722 cm$^{-1}$.

EXAMPLE 19

N-(Benzyloxycarbonyl)ureido-N'-benzyloxycarbonyl-S-methylisothiourea (21)

To a solution of benzyloxycarbonyl-S-methylisothiourea (1.12 g, 5.0 mmol, 1.0 eq) in THF (20 mL) was added benzyloxycarbonylisocyanate (1.06 mL, 6.0 mmol, 1.2 eq) at room temperature. After 20 min, the solvent was evaporated and the residue was triturated in anhydrous ethyl ether twice to afford 2.0 g (100%) of 21 as a white solid. $^1$HNMR (300 MHz, DMSO-d$_6$ vs TMS): δ2.29 (3H, 2), 5.15 (2H, s), 5.22 (2H, s), 7.40 (10H, m) ppm. IR (NaCl, film): 3226, 3159, 2925, 1749, 1715, 1558, 1469, 1261, 1205 cm$^{-1}$; mp: 165–6° C. (recryst. $CH_2Cl_2$/EtOAc): Anal. Calcd. for $C_{10}H_{12}N_2O_2S$: C, 56.85, H, 4.77, N, 10.47, S 7.99. Found: C, 57.00; H, 4.97; N, 10.36; S, 7.76.

EXAMPLE 20

N-Acetyl-N'-butyloxycarbonyl-S-methylisothiourea 78a

To a solution of 77 (350 mg, 1.84 mmol, 1.0 eq) in $CH_2Cl_2$ (5.0 mL) was added acetic anhydride (190 μL/207 mg, 1.1 mmol, 1.1 eq) and TEA (388 μL, 2.76 mmol, 1.5 eq). The mixture was stirred for 16 h at room temperature. The resulting mixture was diluted with $CH_2Cl_2$ (50 mL), washed with brine, dried over $Na_2SO_4$, filtered and concentrated. Purification via column chromatography (silica gel, $CH_2Cl_2$:EtOAc, 9:1) provided 372 mg (87%) of 78a as a semi-solid. $^1$HNMR (300 MHz, $CDCl_3$ vs TMS): δ1.53 (9H, s); 2.39 (3H, a); 12.45 (1H, br, $D_2O$ exchanged) ppm. IR (NaCl, film): 3090, 2986, 2926, 1726, 1650, 1584, 1406, 1291, 1234, 1151 cm$^{-1}$. Anal. Calcd. for $C_9H_{16}N_2O_3S$: C, 45.56; H, 6.94; N, 12.06. Found: C, 46.41; H, 6.99; N, 12.23.

EXAMPLE 21

N-Acetyl-S-methylisothiourea 79a

The 78a (133 mg, 0.57 mmol) was treated with TPA (1.0 mL). The resulting mixture was stirred for 30 min at room temperature, evaporated to dryness and put on vacuum line for 2 h, triturated with anhydrous $Et_2O$ to give 130 mg of 79a as a semi-solid. This crude product was carried on without further purification. $^1$HNMR (300 MHz, $CD_3OD$): δ2.24 (3H, s); 2.71 (3H, s) ppm; IR (NaCl, film): 3265, 2885, 1740, 1650, 1435, 1242, 1188 cm$^{-1}$.

EXAMPLE 22

S-methylisothiourea 71a

To a solution of 27 (278 mg, 0.35 mmol, 1.0 eq), DMAP (115 mg, 0.95 mmol, 2.7 eq) and EDCI.HCl (81 mg, 0.42 mmol, 1.2 eq) in $CH_2Cl_2$ (2.0 mL) was added 79a (130 mg, 0.53 mmol, 1.5 eq). The resulting mixture was stirred overnight at room temperature, then, diluted with $CH_2Cl_2$ and washed with brine, dried over anhydrous $Na_2SO_4$, filtered and concentrated. Purification via column chromatography (silica gel, $CH_2Cl_2$:EtOAc, 7:3) provided 167 mg (52%) of 71a as a semi-solid. $^1$H NMR (300 MHz, $CDCl_3$ vs TMS): δ1.42 (9H, s); 1.71 (4H, m); 2.11 (3H, s); 2.27 (3H, s); 2.52 (2H, m); 2.95 (3H, s); 3.48 (1H, m); 3.71 (1H, m); 3.95 (3H, m); 4.39 (1H, br, $D_2O$ exchanged); 5.04 (2H, s); 5.07 (1H, m); 5.10 (2H, S); 5.22 (2H, s); 7.36 (15H, m); 5.88 (1H, d, J=5.7 Hz, HNCBz); 9.28 (1H, br, $D_2O$ exchanged); 9.43 (1H, br, $D_2O$ exchanged); 12.06/12.19 (1H, br, $D_2O$ exchanged) ppm. IR (NaCl, film): 3382, 2974, 2931, 1713, 1615, 1538, 1503, 1387, 1250, 1096, 1012 cm$^{-1}$. HRMS: Calcd. for ($C_{44}H_{56}N_8O_{11}S$+H)=905.3868. Found: (M+H)= 905.3901.

EXAMPLE 23

Cyclization Product 72a

To a mixture of 71a (90 mg, 0.103 mmol, 1.0 eq) in $CH_2Cl_2$ (0.5 mL) was added TFA (0.5 mL). The resulting mixture was stirred for 15 min at room temperature. The TFA was evaporated and coevaporated with $CH_2Cl_2$ to dryness. The resulting residue was dried on vacuo for 2 h and triturated with ethyl ether to give a white solid. This white solid was dissolved in THF (1.5 mL). To this solution was added triethylamine (30 μL, 0.206 mmol, 2.0 eq). After stirring the solution for 10 min, the solvent was evaporated. Separation via PTLC (silica gel, $CH_2Cl_2$:EtOAc:MeOH, 4:1:0.5) provided 26 mg (32%) of 79a as a colorless oil. $^1$H NMR (300 MHz, $CD_3OD$): δ1.60 (4H, m); 2.18 (3H, s); 2.55 (1.5H, m); 2.83 (½H, d, J=22 Hz); 2.91 (3H, s); 3.28 (1H, m); 3.46 (2H, m); 3.95 (3H, m); 5.07 (2H, m); 5.12 (2H, s); 5.23 (2H, s); 7.35 (15H, m) ppm. IR (NaCl, film): 3385, 3262, 2936, 1713, 1612, 1555, 1501, 1377, 1251, 1098 cm$^{-1}$; HRMS: Calcd. for $(C_{38}H_{44}N_8O_9+H)$=757.3309. Found: (M+H)=757.3299.

EXAMPLE 24

3S,5'S/R-3-amino-6-[(aminoiminomethyl)amino]-N-(2-acetylamino-1,4,5,6-tetrahydro-4-oxo-5-pyrimidinyl)-N-methyl-hexanamide 73a To a solution of 72a (13 mg, 0.016 mmol, 1.0 eq) in MeOH (0.5 mL)/$CH_2Cl_2$ (0.1 mL) was added $PdCl_2$ (13 mg). The reaction flask was charged with $H_2$ from a balloon and the mixture was hydrogenated at 1 atm. of $H_2$ for 15 min. The mixture was then purged with nitrogen and filtered to remove the catalyst. The filtrate was concentrated and dried in vacuo to give a 2HCl salt of 73a (6 mg, 99% yield) as an amorphous solid. $^1$HNMR (300 MHz, $D_2O$): δ1.77 (4H, m); 2.31 (3H, s); 2.87 (1H, m); 3.02 (1H, m); 3.14 (3H, s); 3.27 (2H, t, J=6.3 Hz); 3.70 (1H, m); 3.97 (2H, m); 5.16 (1H, m) ppm; IR (KBr pellet): 3394, 3156, 2913, 1737, 1651, 1591, 1365, 1203, 1138 cm$^{-1}$. HRMS (FAB): Calcd. for $(C_{14}H_{26}N_8O_3+H)$=355.2206, Found (M+H)=355.2204.

EXAMPLE 25

N-Benzoyl-N'-butyloxycarbonyl-S-methylisothiourea 78b

To a solution of 77 (190 mg, 1.0 mmol, 1.0 eq) in $CH_2Cl_2$ (5.0 mL) was added PhCOCl (128 μL/154 mg, 2.0 mmol, 2.0 eq) and TEA (308 μL, 2.2 mmol, 2.2 eq). The mixture was stirred for 16 h at room temperature. The resulting mixture was diluted with $CH_2Cl_2$ (50 mL), washed with brine, dried over $Na_2SO_4$, filtered and concentrated. Purification via column chromatography (silica gel, $CH_2Cl_2$:EtOAc, 4:1) provided 200 mg (68%) of 78b as a white solid. $^1$HNMR (300 MHz, $CDCl_3$ vs TMS): δ1.45 (9H, s); 2.50 (3H, s); 7.39 (3H, m); 8.09 (2H, m); 12.49 (1H, br, $D_2O$ exchanged) ppm. IR (NaCl, film): 3067, 2980, 2929, 1746, 1612, 1538, 1392, 1312, 1280, 1141 cm$^{-1}$. mp: 99–101° C. HRMS: Anal. Calcd. for $(C_{14}H_{18}N_2O_3S+H)$=295.1133. Found: (M+1)=295.1110.

EXAMPLE 26

N-Benzoyl-S-methylisothiourea 79b

To a mixture of 78b (160 mg, 0.54 mmol) and anisole (0.1 mL) was added TFA (1.0 mL). The resulting mixture was stirred for 30 min at room temperature, evaporated to dryness and put on vacuum line for 2 hours, and triturated with anhydrous $Et_2O$ to give 135 mg of 79b as a semi-solid. This crude product was used directly in the next step without further purification. $^1$HNMR (300 MHz, $CD_3OD$): δ2.74 (3H, m); 7.55 (2H, t, J=7.8 Hz); 7.69 (1H, t, J=7.5 Hz); 8.02 (2H, d, J=7.5 Hz) ppm. IR (NaCl, film): 3226, 2936, 1695, 1680, 1540, 1188 cm$^{-1}$.

EXAMPLE 27

Coupling Product 71b

To a solution of 27 (158 mg, 0.20 mmol, 1.0 eq), DMAP (73 mg, 0.6 mmol, 3.0 eq) and EDCLHCl (46 mg, 0.24 mmol, 1.2 eq) in $CH_2Cl_2$ (2 mL) was added 79b (93 mg, 0.5 mmol, 1.2 eq). After stirring overnight at room temperature, the resulting mixture was diluted with $CH_2Cl_2$, washed with brine, dried over anhydrous $Na_2SO_4$, filtered and concentrated. Purification via column chromatography (silica gel, $CH_2Cl_2$:EtOAc, 7:3) provided 39 mg (39%) of 71b as a semi-solid. $^1$HNMR (300 MHz, $CD_3OD$): δ1.42 (9H, B); 1.58 (4H, m); 2.38–2.81 (2H, m); 2.52 (3H, s); 3.11 (3H, s); 3.49 (1H, m); 3.86 (4H, m); 4.70 (1H, m); 4.95 (2H, m); 5.07 (2H, s); 5.16 (2H, m); 7.34 (15H, m); 7.51 (2H, m); 7.88 (1H, m); 8.21 (2H, m) ppm; IR (NaCl, film): 3388, 2974, 1715, 1608, 1538, 1454, 1392, 1249, 1171, 1099 cm$^{-1}$. HRMS (FAB): Calcd. $(C_{49}H_{58}N_8O_{11}S+H)$=967.4024, Found (M+H)=967.4051.

EXAMPLE 28

Cyclization Product 72b

To a mixture of 71b (45 mg, 0.042 mmol, 1.0 eq) in $CH_2Cl_2$ (0.5 mL) is added TFA (0.5 mL). The resulting mixture was stirred for 15 min at room temperature. The TFA was evaporated and coevaporated with $CH_2Cl_2$ to dryness. The resulting residue was dried on vacuo for 2 hours and triturated with dry ether to give a white solid. This white solid was dissolved in THF (1.0 mL). To this solution was added triethylamine (20 μL, 0.136 mmol, 4.0 eq). After stirring the solution for 10 min, the solvent was evaporated and the resulting residue was purified on PTLC (silica gel, $CH_2Cl_2$:EtOAc:MeOH, 4:1:0.5) to give 4 mg (10%) of 72b as a colorless oil. $^1$HNMR (300 MHz, $CD_3OD$): δ1.62 (4H, m); 2.56 (2H, m); 3.02 (3H, s); 3.37 (1H, m); 3.70 (1H, m); 3.93 (3H, m); 5.02 (3H, m); 5.12 (2H, s); 5.25 (2H, s); 7.32 (18H, m); 8.15 (2H, d, J=7.2 Hz) ppm; IR (NaCl, film): 3385, 3263, 3056, 2927, 1720, 1633, 1505, 1454, 1378, 1322, 1253, 1094, 1063 cm$^{-1}$; HRMS (FAB): Calcd. $(C_{43}H_{46}N_8O_9+H)$=819.3466, Found (M+H)=819.3436.

EXAMPLE 29

3S,5'6/R-3-amino-6-[(aminoiminomethyl)amino]-N-(2-benzoylamino-1,4,5,6-tetrahydro-4-oxo-5-pyrimidinyl)-N-methyl-hexanamide 73b To a solution of 72b (3 mg, 0.003 mmol, 1.0 eq) in MeOH (0.5 mL)/$CH_2Cl_2$ (0.1 mL) was added $PdCl_2$ (5 mg). The reaction flask was charged with $H_2$ from a balloon and the mixture was hydrogenated at 1 atm. of $H_2$ for 15 minutes. The mixture was then purged with nitrogen and filtered to remove the catalyst. The filtrate was concentrated and dried in vacuo to give a 2HCl salt of 73b (2 mg, 99%) as a colorless, amorphous solid. $^1$HNMR (300 MHz, $D_2O$): δ1.76 (4H, m); 2.85 (1H, m); 3.02 (1H, m); 3.18 (3H, s); 3.26 (2H, t, J=5.4 Hz); 3.69 (1H, m); 4.05 (2H, m); 5.18 (1H, dd, J=8.7 Hz); 7.62 (2H, t, J=7.2 Hz); 7.77 (1H, t, J=6.6 Hz), 7.98 (1H, d, J=7.2 Hz) ppm; IR (NaCl, film): 3398, 2935, 1732, 1650, 1411, 1259 cm$^{-1}$. HRMS (FAB): Calcd. $(C_{19}H_{28}N_8O_2+H)$=417.2363, Found (M+H)=417.2371.

EXAMPLE 30

N-Methylcarbonyl-N'-butyloxycarbonyl-S-methylisothiourea 78c

To a solution of 77 (190 mg, 1.0 mmol, 1.0 eq) in $CH_2Cl_2$ (5.0 mL) was added methyl chloroformate (170 μL/208 mg, 2.2 mmol, 2.2 eq) and TEA (842 μL, 6.0 mmol, 6.0 eq). The mixture was stirred for 16 hours at room temperature. The resulting mixture was diluted with $CH_2Cl_2$ (50 mL), washed with brine, dried over $Na_2SO_4$, filtered and concentrated. Purification via column chromatography (silica gel, $CH_2Cl_2$:EtOAc, 4:1) provided 150 mg (60%) of 78c as an oil. $^1$HNMR (300 MHz, $CDCl_3$ vs TMS): δ1.50 (9H, s); 2.41 (3H, s); 3.79 (3H, s); 11.59 (1H, br, $D_2O$ exchanged) ppm. IR (NaCl, film): 3466, 3187, 1981, 1748, 1659, 1651, 1574, 1416, 1254, 1145 $cm^{-1}$. HRMS: Anal. Calcd. for $(C_9H_{16}N_2O_4S+H)$=249.0926. Found: (M+1)=249.0916.

EXAMPLE 31

N-Methylcarbonyl-S-methylisothiourea 79c

To a mixture of 78c (140 mg, 0.55 mmol) and anisole (0.1 mL) was added TFA (1.0 mL). The resulting mixture was stirred for 30 min at room temperature, evaporated to dryness, put on vacuum line for 2 hours and, triturated with anhydrous $Et_2O$ to give 140 mg of product as a semi-solid. This crude 79c was carried on without further purification. $^1$HNMR (300 MHz, $CD_3OD$): δ2.70 (3H, s); 3.88 (3H, s) ppm. IR (NaCl, film): 3387, 3283, 3012, 2930, 1672, 1589, 1505, 1433, 1257, 1112 $cm^{-1}$.

EXAMPLE 32

Coupling Product 71c

To a solution of 27 (320 mg, 0.40 mmol, 1.0 eq), DMAP (146 mg, 1.2 mmol, 3.0 eq) and EDCLHCl (96 mg, 0.5 mmol, 1.2 eq) in $CH_2Cl_2$ (2 mL) was added 79c (131 mg, 0.5 mmol, 1.2 eq). After stirring overnight at room temperature, the resulting mixture was diluted with $CH_2Cl_2$, washed with brine, dried over anhydrous $Na_2SO_4$, filtered and concentrated. Purification via column chromatography (silica gel, $CH_2Cl_2$:EtOAc, 7:3) provided 141 mg (38%) of 72c as a semi-solid. $^1$HNMR (300 MHz, $CD_3OD$): δ1.44 (9H, s); 1.63 (4H, m); 2.31 (3H, s); 2.60 (2H, m); 3.04 (3H, s); 3.42 (1H, m); 3.66/3.67 (3H, s); 3.70 (1H, m); 3.93 (3H, m); 4.67 (1H, m); 5.01 (2H, s); 5.10 (2H, s); 5.24 (2H, s); 7.31 (15H, m) ppm; IR (NaCl, $CH_2Cl_2$): 3389, 2959, 1715, 1254, 1171, 1099 $cm^{-1}$. HRMS (FAB): Calcd. $(C_{44}H_{56}N_8O_{12}S+H)$=921.3817. Found (M+H)=921.3834.

EXAMPLE 33

Cyclization Product 72c

To a mixture of 71c (46 mg, 0.05 mmol, 1.0 eq) in $CH_2Cl_2$ (0.5 mL) was added TFA (0.5 mL). The resulting mixture was stirred for 15 min. The TFA was evaporated and coevaporated with $CH_2Cl_2$ to dryness. The resulting residue was dried on vacuo for 2 hours and triturated with dry ether to give a white solid. This white solid was dissolved in THF (1.0 mL). To this solution was added triethylamine (15 μL, 0.1 mmol, 2.0 eq). After stirring for 10 min, the solvent was evaporated and the resulting residue was purified on PTLC (silica gel, $CH_2Cl_2$:EtOAc:MeOH, 4:1:0.5) to give 9 mg (22%) of 72c as a colorless oil. $^1$HNMR (300 MHz, $CD_3OD$): δ1.60 (4H, m); 2.48 (1H, m); 2.57 (1H, m); 2.87/2.93 (3H, s); 3.02 (1H, m); 3.27 (1H, m); 3.31 (3H, s); 3.94 (3H, m); 4.82 (1H, m); 5.02 (2H, s); 5.11 (2H, s); 5.25 (2H, s); 7.30 (15H, m) ppm; IR (NaCl, film): 3377, 2917, 1722, 1642, 1512, 1256, 1092 $cm^{-1}$. HRMS (FAB): Calcd. $(C_{38}H_{44}N_8O_{10}+H)$=773.3266, Found (M+H)=773.3259.

EXAMPLE 34

3S,5'S/R-3-amino-6-[(aminoiminomethyl)amino]-N-(2-methoxycarbonylamino-1,4,5,6-tetrahydro-4-oxo-5-pyrimidinyl)-N-methyl-hexanamide 73c To a solution of 72c (9 mg, 0.012 mmol, 1.0 eq) in MeOH (0.5 mL)/$CH_2Cl_2$ (0.1 mL) was added $PdCl_2$ (10 mg). The reaction flask was charged with $H_2$ from a balloon and the mixture was hydrogenated at 1 atm. of $H_2$ for 15 min. The mixture was then purged with nitrogen and filtered to remove the catalyst. The filtrate was concentrated and dried in vacuo to give a 2HCl salt of 73c (5 mg, 97%) as a white amorphous solid. $^1$HNMR (300 MHz, $D_2O$): δ1.76 (4H, m); 2.85 (1H, m); 3.01 (1H, m); 3.15 (3H, s); 3.26 (2H, t, J=6 Hz); 3.69 (1H, m); 3.86 (3H, s); 3.98 (2H, m); 5.13 (1H, m) ppm; IR (KBr, pellet): 3430, 3379, 2948, 1762, 1642, 1213, 1134 $cm^{-1}$. HRMS (FAB): Calcd. $(C_{14}H_{26}N_8O_4+H)$=371.2155, Found (M+H)=371.2170.

EXAMPLE 35

N-Methylsulfonyl-N'-butyloxycarbonyl-S-methylisothiourea 78d

To a solution of 77 (380 mg, 2.0 mmol, 1.0 eq) in $CH_2Cl_2$ (5.0 mL) was added $CH_3SO_2Cl$ (310 μL/458 mg, 2.0 mmol, 2.0 eq) and TEA (842 μL, 6.0 mmol, 3.0 eq). The mixture was stirred for 2 hours at room temperature. The resulting mixture was diluted with $CH_2Cl_2$ (50 mL), washed with brine, dried ($Na_2SO_4$), filtered and concentrated. Purification via column chromatography (silica gel, $CH_2Cl_2$:EtOAc, 4:1) provided 500 mg (93%) of 78d as a yellow oil. $^1$HNMR (300 MHz, $CDCl_3$ vs TMS): δ1.50 (9H, s); 2.34 (3H, s); 3.09 (3H, s); 10.05 (1H, br, $D_2O$ exchanged) ppm. IR (NaCl, film): 3242, 2981, 2934, 1752, 1572, 1455, 1371, 1298, 1234, 1154, 1115 $cm^{-1}$. HRMS: Anal. Calcd. for $(C_8H_{16}N_2O_4S_2+H)$=269.0663. Found: (M+1)=269.0623.

EXAMPLE 36

N-Methylsulfonyl-S-methylisothiourea 79d

To a mixture of 78d (300 mg, 1.12 mmol) and anisole (0.1 mL) was added TFA (1.0 mL). The resulting mixture was stirred for 30 min at room temperature, evaporated to dryness, put on vacuum line for 2 hours, triturated with anhydrous $Et_2O$ to give 300 mg of 78d as semi-solid. This crude product was carried on without further purification. $^1$HNMR (300 MHz, $CD_3OD$): δ2.42 (3H, s); 3.05 (3H, s) ppm. IR (NaCl, film): 3405, 3306, 2925, 1622, 1540, 1340, 1266, 1119 $cm^{-1}$.

EXAMPLE 37

Coupling Product 71d

To a solution of 27 (237 mg, 0.30 mmol, 1.0 eq), DMAP (110 mg, 0.9 mmol, 3.0 eq) and EDCLHCl (61 mg, 0.36 mmol, 1.2 eq) in $CH_2Cl_2$ (2 mL) was added 79d (102 mg, 0.5 mmol, 1.2 eq). After stirring overnight at room temperature, the resulting mixture was diluted with $CH_2Cl_2$, washed with brine, dried over anhydrous $Na_2SO_4$, filtered and concentrated. Purification via column chromatography (silica gel, $CH_2Cl_2$:EtOAc, 7:3) provided 97 mg (34%) of 71d as a semi-solid. $^1$HNMR (300 MHz, $CD_3OD$): δ1.39 (9H, s); 1.64 (4H, m); 2.29 (3H, s); 2.51–2.76 (2H, m); 3.00 (6H, s); 3.40 (1H, m); 3.64 (1H, m); 3.93 (3H, m); 4.55 (1H, m); 5.01 (2H, s); 5.11 (2H, s); 5.24 (2H, s); 7.29 (15H, m) ppm; IR (NaCl, film): 3388, 2976, 2498, 1714, 1688, 1504, 1416, 1251, 1113 $cm^{-1}$. HRMS (FAB): Calcd. for $(C_{43}H_{56}N_8O_{12}S_2+H)$=941.3537, Found (M+H)=941.3533.

EXAMPLE 38

Cyclization Product 72d

To a mixture of 71d (38 mg, 0.04 mmol, 1.0 eq) in $CH_2Cl_2$ (1 mL) was added anisole (10 μL) and TFA (1 mL). The resulting mixture was stirred for 15 min. The TFA was evaporated and coevaporated with $CH_2Cl_2$ to dryness. The resulting residue was dried on vacuo for 2 h and triturated with dry ether to give a white solid. This white solid was dissolved in THF (1.0 mL). To this solution was added triethylamine (22 µL, 0.16 mmol, 4.0 eq). After stirring the solution for 10 min, the solvent was evaporated and the resulting residue was purified on PTLC (silica gel, $CH_2Cl_2$:EtOAc:MeOH, 4:1:0.5) to give 28 mg (88%) of 72d as a colorless oil. $^1$HNMR (300 MHz, $CD_3OD/CDCl_3$ vs TMS): δ1.50 (2H, m); 1.63 (2H, m); 2.52 (2H, m); 2.95 (3H, s); 2.97 (3H, s); 3.25 (1H, m); 3.57 (1H, m); 3.90 (3H, m); 4.80 (1H, m); 5.02 (2H, m); 5.09 (2H, m); 5.22 (2H, s); 7.29 (15H, m) ppm; IR (NaCl, film): 3392, 3286, 2940, 1846, 1716, 1506, 1456, 1377, 1254, 1108, 1003, 907 cm$^{-1}$; HRMS (FAB): Calcd. $(C_{37}H_{44}N_8O_{10}S+H)=793.2979$, Found (M+H)=793.3012.

EXAMPLE 39

3S,5'S/R-3-amino-6-[(aminoiminomethyl)amino]-N-(2-methylsulfonylamino-1,4,5,6-tetrahydro-4-oxo-5-pyrimidinyl)-N-methyl-hexanamide 73d To a solution of 72d (28 mg, 0.035 mmol, 1.0 eq) in MeOH (1 mL)/$CH_2Cl_2$ (0.3 mL) was added $PdCl_2$ (12 mg). The reaction flask was charged with $H_2$ from a balloon and the mixture was hydrogenated at 1 atm. of $H_2$ for 15 min. The mixture was then purged with nitrogen and filtered to remove the catalyst. The filtrate was concentrated and dried in vacuo to give a 2HCl salt of 73d (16 mg, 99%) as a colorless semi-solid. $^1$HNMR (300 MHz, $D_2O$): δ1.76 (4H, m); 2.84 (1H, m); 3.00 (1H, m); 3.12 (3H, s); 3.13 (3H, s); 3.26 (2H, t, J=5.7 Hz); 3.69 (1H, m); 3.76 (1H, m); 3.86 (1H, m); 5.01 (1H, m) ppm; IR (KBr pellet): 3411, 3156, 2933, 1733, 1639, 1373, 1261, 1100 cm$^{-1}$; HRMS (FAB): Calcd. for $(C_{13}H_{26}N_8O_4+H)=391.1876$, Found (M+H)=391.1885.

EXAMPLE 40

S methylisothiourea 71e

To a solution of 27 (120 mg, 0.15 mmol, 1.0 eq), DMAP (37 mg, 0.3 mmol, 2.0 eq) and EDCL.HCl (32 mg, 0.16 mmol, 1.1 eq) in $CH_2Cl_2$ (0.5 mL) was added 79e (50 mg, 0.23 mmol, 1.5 eq) (79e was prepared in accordance with the procedure described by Tian, et al. Int. J. Peptide Protein Res. 1992, 40, 119–126). The resulting mixture was stirred overnight at room temperature, then, diluted with $CH_2Cl_2$, washed with brine, dried over anhydrous $Na_2SO_4$, filtered and concentrated. Purification via column chromatography (silica gel, $CH_2Cl_2$:EtOAc, 7:3) provided 70 mg (52%) of 71e as a semi-solid. $^1$HNMR (300 MHz, $CD_3OD$): δ1.40 (9H, s); 1.61 (4H, m); 2.32 (3H, s); 2.51 (1H, m); 2.77 (1H, m); 3.02/3.04 (3H, s); 3.40 (1H, m); 3.68 (1H, m); 3.91 (3H, m); 4.61 (½H, m); 4.74 (½H, m); 4.99/5.00 (2H, s); 5.08 (4H, s); 5.21 (2H, s); 7.27 (20H, m) ppm. IR (NaCl, film): 3388, 2976, 1715, 1650, 1609, 1505, 1416, 1254, 1172, 1100 cm$^{-1}$. HRMS (FAB): Calcd. for $(C_{50}H_{60}N_8O_{12}S+H)=997.4146$, Found (M+H)=997.4111.

EXAMPLE 41

Cyclization Product 72e

To a mixture of 71e (40 mg, 0.040 mmol, 1.0 eq) and anisole (20 µL) in $CH_2Cl_2$ (1.0 mL) was added TFA (1.0 mL). The resulting mixture was stirred for 20 min at 0° C. The TFA was evaporated and coevaporated with $CH_2Cl_2$ to dryness. The resulting residue was dried on vacuo for 2 h and triturated with ethyl ether to give a white solid. This white solid was dissolved in $CH_2Cl_2$ (1.0 mL). To this solution was added triethylamine (12 µL, 0.04 mmol, 2.0 eq). After stirring the solution for 10 min, the solvent was evaporated. Separation via PTLC (silica gel, $CH_2Cl_2$:EtOAc:MeOH, 4:1:0.5) provided 17 mg (50%) of 72e as a colorless oil. $^1$HNMR (300 MHz, $CD_3OD$): δ1.52 (4H, m); 2.54 (2H, m); 2.98 (3H, s); 3.56 (2H, m); 3.92 (3H, m); 5.05 (3H, m); 5.11 (2H, s); 5.15 (2H, s); 5.25 (2H, s); 7.31 (20H, m) ppm. IR (NaCl, film): 3384, 3272, 2925, 1722, 1645, 1514, 1503, 1254, 1084 cm$^{-1}$. HRMS (FAB): Calcd. for $(C_{44}H_{48}N_8O_{10}+H)=849.3571$, Found (M+H)=849.3571.

EXAMPLE 42

3S,5'S/R-3-amino-6-[(aminoiminomethyl)amino]-N-(2-amino-1,4,5,6-tetrahydro-4-oxo-5-pyrimidinyl)-N-methyl-hexanamide 73e To a solution of 72e (12 mg, 0.014 mmol, 1.0 eq) in MeOH (1.0 mL)/$CH_2Cl_2$ (0.2 mL) was added $PdCl_2$ (10 mg). The reaction flask was charged with $H_2$ from a balloon and the mixture was hydrogenated at 1 atm. of $H_2$ for 20 min. The mixture was then purged with nitrogen and filtered to remove the catalyst. The filtrate was concentrated and dried in vacuo to give a 3HCl salt of 73e (6 mg, 99% yield) as an amorphous solid. $^1$HNMR (300 MHz, $D_2O$ vs DOH): δ1.76 (4H, m); 2.83 (1H, m); 3.01 (1H, m); 3.13 (3H, s); 3.26 (2H, t, J=5.1 Hz); 3.69 (1H, m); 3.78 (1H, m); 3.87 (1H, m); 5.06 (1H, m) ppm; IR (KBr pellet): 3367, 3167, 2922, 1728, 1711, 1650, 1500, 1217, 1156 cm$^{-1}$. HRMS (FAB): Calcd. $(C_{12}H_{24}N_8O_2+H)=313.2094$, Found (M+H)=313.2100.

As indicated hereinabove, the compounds of the present invention exhibit anti-bacterial activity, as shown in the following example.

EXAMPLE 43

Test compounds were assayed against *Staphylococcus aureus* FDA 209P by the 10 fold agar disc diffusion assay on BHI-plates at pH=7 and pH=9 in accordance with the procedure from the National Committee for Clinical Laboratory Standards 1989. Susceptibility testing. A panel of 16 bacteria was used to evaluate the antimicrobial activity of the compounds (Table 2). The MIC of each antimicrobial agent was determined using a microdilution method according to NCCLS standards[1]. Serial twofold dilutions of antibiotics were prepared in Mueller-Hinton broth (Difco Laboratories, Detroit, Mich.). Bacteria were grown to early log phase at 35° C. (1 hours) in Mueller-Hinton broth and cultures were diluted to achieve a final inoculum of 5×10$^5$ CFU per ml. Microtiter plates were incubated at 35° C. for 20 h and then were read using a Thermo$_{Max}$ microplate reader (Molecular Devices, Sunnyvale, Calif.) and a microtiter plate reading mirror. The MIC was defined as the lowest concentration of antibiotic which inhibited the development of visible growth at the end of the incubation period. The standard reference strains were *Staphyloccocus aureus* ATCC 292132, *Enterococcus faecalis* ATCC 29212, *E. faecium* ATCC 35667, *Escherichia coli* ATCC 25922, and *Pseudomonas aeruginosa* ATCC 27853. Imipenem and vancomycin were used as antibiotic controls and values for reference strains were in accordance with the NCCLS.

[1] Arthur, M., C. Molinas, F. Deparideu, and P. Courvalin. 1993. Characterization of Tn 1546, a Tn-3 related transposon conferring glycopeptide resistance by synthesis of depsipeptide peptidogycan precursors in *Enterococcus faecium* BM4147. J. Bacteriol. 175: 117–127.

TABLE 2

Panel of bacteria for susceptibility testing

| BACTERIA | SOURCE OF REFERENCE | COMMENTS |
|---|---|---|
| *Staphylococcus aureus* ATCC 29213 | ATCC | Reference strain |
| *Staphylococcus aureus* COL8A | [4] | Methicillin susceptible, isogenic to COL |
| *Staphylococcus aureus* PC1 | [6] | Type A β-lactamase hyperproducer |
| *Staphylococcus aureus* sa ATCC 13709 | ATCC | Smith strain |
| *Staphylococcus aureus* COL | [5] | Methicillin resistant, β-lactamase negative |
| *Staphylococcus aureus* 76 | [8] | Methicillin resistant, β-lactamase positive |
| *Staphylococcus aureus* ATCC 33593 | ATCC | Methicillin resistant, β-lactamase positive |
| *Staphylococcus aureus* sa201 | Clinical isolate, Spain | Methicillin resistant, β-lactamase positive |
| *Staphylococcus haemolyticus* UA281 | [3] | Methicillin resistant |
| *Enterococcus faecalis* ATCC 29212 | ATCC | Reference strain |
| *Enterococcus faecium* ATCC 35667 | ATCC | Reference strain |
| *Enterococcus faecium* BM4147 | [1] | Vancomycin resistant, vanA |
| *Enterococcus faecalis* V583 | [3] | Vancomycin resistant, vanB |
| *Enterococcus faecium* efm040 | Clinical isolate, USA | Ampicillin resistant |
| *Escherichia coli* ATCC 25922 | ATCC | Reference strain |
| *Pseudomonas Aeruginosa* ATCC 27853 | ATCC | Reference strain |

1. Arthur, M., C. Molinas, F. Deparideu, and P. Courvalin. 1993. Characterization of Tn1546, a Tn3-related transposon conferring glycopeptide resistance by synthesis of depsipeptide peptidogycan precursors in *Enterococcus faecium* BM4147. J. Bacteriol. 175:117–127.

2. Courvalin P., J. P. Flandrois, F. Goldstein, A. Philippon, C. Quentin, J. Sirot. 1985. L'antibiogramme automatise. Souchier No. 1. Ire Edition. Vigot.

3. Evers, S., D. F. Sahm, and P. Courvalin. 1993. The vanβ gene of vancomycin-resistant *Enterococcus faecalis* V583 is structurally related to genes encoding D-Ala-D-Ala ligases and glycopeptide-resistance proteins VanA and VanC. Gene 124:143–144.

4. Gerberding, J. L., C. Miick, H. H. Liv, and H. F. Chambers 1991. Comparison of conventional susceptibility tests with directed detection of penicillin-binding protein 2a in borderline oxacillin-resistant strains of *Staphylococcus aureus*. Antimibrob. Agents Chemother. 35:2574–2579.

5. Hartman, B. J. and A. Tomasz. 1984. Low-affinity penicillin-binding protein associated with beta-lactam resistance in *Staphylococcus aureas*. J. Bacteriol. 158:513–516.

6. Kernodle, D. S., D. J. Zygmunt, P. A. McGraw and J. R. Chipley. 1990. Purification of *Staphylococcus aureus* b-lactamases by using sequential cation-exchange and affinity chromatography. Antimicrob. Agents Chemother. 34: 2177–2183.

7. National committee for Clinical Laboratory Standards (NCCLS). 1997. Methods for Dilution of Antimicrobial Susceptibility Tests for Bacteria that grow acrobically-Fourth Edition; Approved Standard. NCCLS Document M7-A4, Vol. 17 No. 2.

8. Peacock, J. E., F. J. Marsik, and R. P. Wenzel. 1980. Methicillin-resistant *Staphylococcus aureus:* introduction and spread within a hosptial. Ann. Intern. Med. 93:526–532.

The data are indicated hereinbelow in Table 3 using representative compounds of the present invention.

The results are indicated hereinbelow:

TABLE 3

Minimal Inhibitory Concentrations (MIC's in µg/mL) of TAN-1057 and analogs.

| BACTERIA | TAN-1057A | 73a | 73c | Imipenem* | Vancomycin* |
|---|---|---|---|---|---|
| *Staphylococcus aureus* ATCC 29213 | 16 | 16 | 64 | ≦0.25 | ≦0.25 |
| *Staphylococcus aureus* COL8A | 16 | 16 | 64 | ≦0.25 | ≦0.25 |
| *Staphylococcus aureus* PC1 | 8 | 8 | 32 | ≦0.25 | ≦0.25 |
| *Staphylococcus aureus* sa ATCC 13709 | 16 | 16 | 32 | ≦0.25 | ≦0.25 |
| *Staphylococcus aureus* COL | 16 | 16 | 64 | 32 | 1 |
| *Staphylococcus aureus* 76 | 16 | 16 | 64 | 8 | ≦0.25 |
| *Staphylococcus aureus* ATCC 33593 | 16 | 8 | 64 | 8 | 0.5 |
| *Staphylococcus aureus* sa201 | 16 | 16 | 64 | 64 | 0.5 |

TABLE 3-continued

Minimal Inhibitory Concentrations (MIC's in µg/mL) of TAN-1057 and analogs.

| BACTERIA | TAN-1057A | 73a | 73c | Imipenem* | Vancomycin* |
|---|---|---|---|---|---|
| *Staphylococcus haemolyticus* UA281 | 32 | 128 | 256 | 64 | 1 |
| *Enterococcus faecalis* ATCC 29212 | 32 | 32 | 64 | 0.5 | 1 |
| *Enterococcus faecium* ATCC 35667 | 32 | 64 | 128 | 4 | ≦0.25 |
| *Enterococcus faecium* BM4147 | 32 | 128 | 64 | 8 | >128 |
| *Enterococcus faecalis* V583 | nd | nd | 64 | 0.5 | 16 |
| *Enterococcus faecium* efm040 | 128 | 256 | >256 | >128 | ≦0.25 |
| *Escherichia coli* ATCC 25922 | 256 | 128 | >256 | ≦0.25 | >128 |
| *Pseudomonas Aeruginosa* ATCC 27853 | 256 | 256 | >256 | 1 | >128 |
| solvent | H$_2$O/DMSO | H$_2$O/DMSO | Methanol | H$_2$O | H$_2$O |

*Control values in accordance with National Committee for Clinical Laboratory Standards (NCCLS)

Bacteria strains 1–14 in Table 2 are gram positive bacteria. The MSSA organisms are methicillin-sensitive strains, while the MRSA organisms are methicillin-resistant strains. The organism listed in item 12 is a methicillin-resistant *Enterococcus faecalis* which is not susceptible to treatment with vancomycin. Bacteria strains 15 and 16 are gram negative organisms.

As clearly seen by the data, the tested compounds exhibit significant anti-bacterial activity.

Thus, the compounds of the present invention inhibit the growth of pathogenic microorganisms, e.g., bacteria. They also inhibit tumor growth. Thus, they are useful as therapeutic agents for the treatment of animals, including mammals, infected with infectious disease caused by pathogenic microorganisms. They also are useful for the treatment of tumors, especially solid tumors, in animals, including mammals.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A compound of the formula:

[chemical structure]

or pharmaceutically acceptable salts thereof, wherein $R_2$ is

[chemical structure showing C(=O)—R]

—R;

R is hydrogen, lower alkyl, aryl, lower arylalkyl, lower alkoxy, lower arylalkoxy or aryloxy;

$R_3$ and $R_4$ are independently hydrogen or lower alkyl;

$R_1$ is [chemical structures shown]

-continued

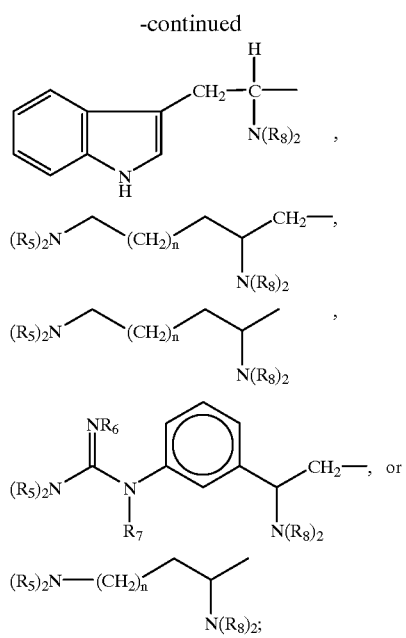

each $R_5$ is the same or different and is hydrogen or lower alkyl;

each $R_8$ is the same or different and is hydrogen or lower alkyl;

$R_6$ and $R_7$ are independently hydrogen or lower alkyl, and n is 1–5.

2. The compound according to claim 1 wherein R is lower alkoxy or lower alkyl.

3. The compound according to claim 1 wherein $R_4$ is lower alkyl.

4. The compound according to claim 3 wherein $R_4$ is $CH_3$.

5. The compound according to claim 1 wherein $R_3$ is hydrogen.

6. The compound according to claim 1 wherein n is 1.

7. The compound according to claim 1 wherein $R_1$ is

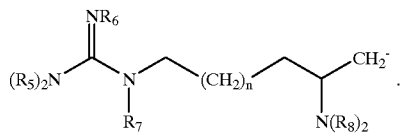

8. The compound according to claim 6 wherein $R_5$, $R_6$, $R_7$ and $R_8$ are all hydrogen.

9. The compound according to claim 7 wherein n is 1.

10. The compound according to claim 1 wherein

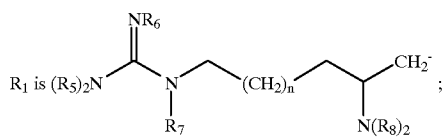

$R_5$, $R_6$, $R_7$ and $R_8$ are hydrogen;
n is 1;

$R_2$ is

R is lower alkyl or lower alkoxy;
$R_3$ is hydrogen; and
$R_4$ is lower alkyl.

11. The compound according to claim 10 wherein $R_2$ is

and $R_4$ is $CH_3$.

12. A pharmaceutical composition comprising a pharmaceutically effective amount of a compound according to any one of claims 1–11 and a pharmaceutical carrier therefor.

13. An anti bacterial agent which comprises an antibiotically effective amount of a compound according to any one of claims 1–11 and a pharmaceutical carrier therefor.

14. An anti-tumor agent for inhibiting the growth of tumorous cells which comprises an anti-tumor effective amount of a compound according to any one of claims 1–11 and a pharmaceutical carrier therefor.

15. A method for treating an bacterial infection in an animal comprising administering to said animal an antibiotically effective amount of a compound according to any one of claims 1–11.

16. The method according to claim 15 wherein the bacterial infection is an infection by a methicillin-resistant strain of bacteria.

17. The method according to claim 15 wherein the bacterial infection is an infection by a methicillin-sensitive strain of bacteria.

18. The method according to claim 15 wherein the bacterial infection is an infection by a methicillin-resistant *Staphylococcus aureus*.

19. The method according to claim 15 wherein the bacterial infection is an infection by a methicillin-sensitive *Staphylococcus aureus*.

20. The method according to claim 15 wherein the bacterial infection is an infection by a bacteria which is a gram positive bacteria.

21. The method according to claim 15 wherein the bacterial infection is an infection by a bacteria which is a gram negative bacteria.

22. A process for forming a compound of the formula:

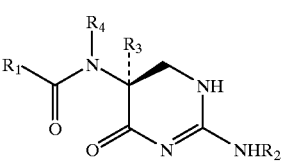

or pharmaceutically acceptable salts thereof, which comprises:

(a) reacting a protected amino acid of the formula

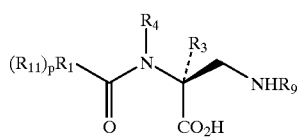

with a compound of the formula

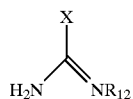

in the presence of a dehydrating coupling agent under amide forming conditions to form a product of the formula:

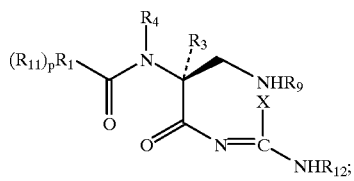

(b) reacting the product of step (a) under conditions effective to remove the protecting group $R_9$ but leaving $R_{11}$ and $R_{12}$ intact, and then reacting the product thereof with effective amounts of base to effect intramolecular cyclization and form the cyclic amidinourea of the formula

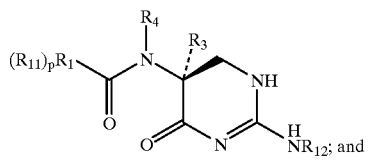

(c) removing the protecting group $R_{11}$, and if $R_{12}$ is other than $R_2$, converting $R_{12}$ to $R_2$;

wherein

CR

R is hydrogen, lower alkyl, aryl, lower arylalkyl, lower alkoxy, lower arylalkoxy, aryloxy or amino;

$R_3$ and $R_4$ are independently hydrogen or lower alkyl;

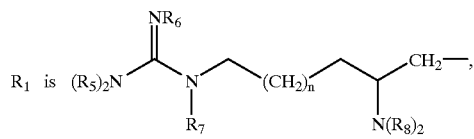

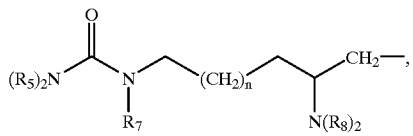

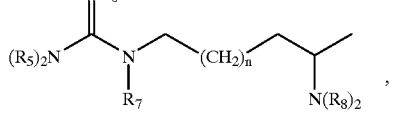

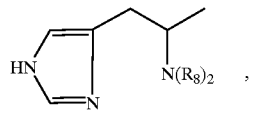

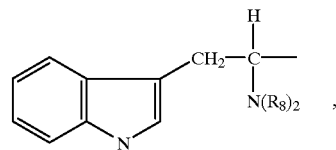

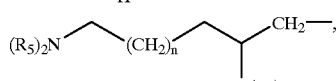

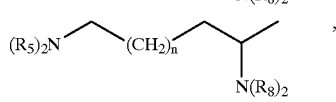

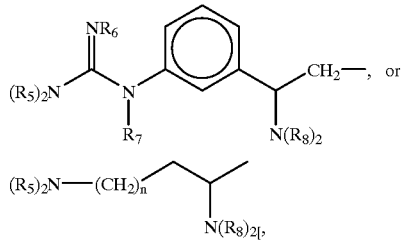

each $R_5$ is the same or different and is hydrogen or lower alkyl;

each $R_8$ is the same or different and is hydrogen or lower alkyl;

$R_6$ and $R_7$ are independently hydrogen or lower alkyl;

n is 1–5;

p is 1–3;

$R_9$ is an amino protecting group;

$R_{11}$ is an amino protecting group different from $R_9$, with the $R_{11}$ group being removed under conditions in which the $R_9$ group is stable and the $R_9$ group being removed under conditions in which the $R_{11}$ group is stable;

$R_{12}$ is $R_2$ or an amino protecting group which is different from $R_9$ and which is the same or different from $R_{11}$ so that when said $R_{12}$ group is an amino protecting group, it is removed under conditions in which the $R_9$ group is stable and the $R_9$ group is removed under conditions in which the $R_{12}$ group is stable;

X is $SR_{10}$, $OR_{10}$, halide, $SO_2R_{10}$, S-heter or a nitrogen containing heteroaromatic containing 5 to 10 ring carbon atoms and at least 1 ring nitrogen atom, said heteroaromatic may be monocyclic or bicyclic;

$R_{10}$ is lower alkyl, aryl or lowerarylalkyl; and heter is a nitrogen containing heteroaromatic containing 6 or 10 ring atoms, the heteroaromatic ring contains 1, 2 or 3 heteroatoms, and the ring heteroatoms are nitrogen.

23. The process according to claim 22 wherein the compound has the formula:

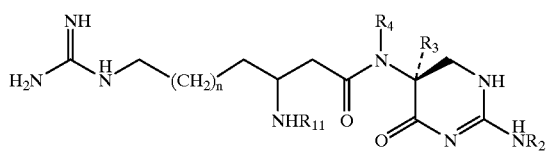

and the compound is formed by the method comprising (a) reacting a protected guanidine of the following formula having protecting groups $R_9$ and $R_{11}$ thereon

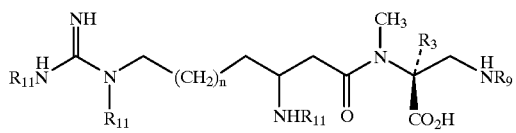

with a thiourea of the formula

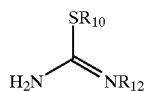

in the presence of a dehydrating coupling agent under effective coupling conditions to form a product of the formula

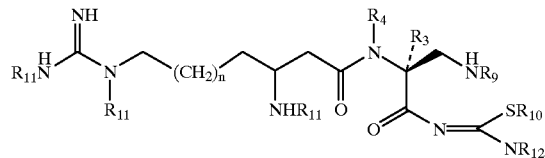

(b) reacting the product of step (a) under conditions effective to remove the protecting group $R_9$ but leaving $R_{11}$ and $R_{12}$ intact, and then reacting the product thereof with effective amounts of base to effect intramolecular cyclization and form the cyclic amidinourea of the formula:

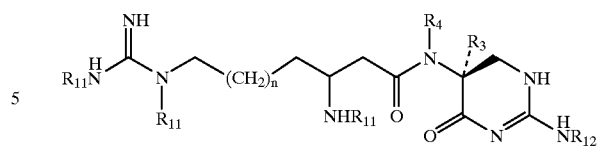

(c) removing the protecting group $R_{11}$, and if $R_{12}$ is a protecting group, then converting $R_{12}$ to $R_2$.

24. The process according to claim 22 or 23 wherein the $R_9$ protecting group is removed by acid and the $R_{11}$ protecting group is removed by hydrogenation.

25. The process according to claim 24 wherein $R_{11}$ is CBZ and $R_9$ is BOC.

26. The process according to claim 22 or 23 wherein R is lower alkyl or lower alkoxy; and $R_3$ is hydrogen and n is 1.

27. The process according to claim 22 wherein $R_4$ is lower alkyl, $R_3$ is hydrogen, $R_1$ is loweralkyl or lower alkoxy, and n is 1.

28. The process according to claim 22 or 23 wherein the base is an hydrocarbyl amine.

29. The process according to claim 28 wherein the base is a tertiary amine.

30. The process according to claim 29 wherein the base is $Et_3N$.

31. The process according to claim 22 wherein the base is present in amounts ranging from about ½ mole to about 2 moles per each mole of protected amino acid.

32. The process according to claim 23 wherein the base is present in amounts ranging from about ½ mole to about 2 moles per each mole of protected guanidine.

33. The process according to claim 22 or 23 wherein the base has the formula:

$R_{21}R_{22}R_{23}N$ wherein $R_{21}$, $R_{22}$ and $R_{23}$ are the same or are different and are hydrogen or lower alkyl.

34. The process according to claim 33 wherein $R_{21}$, $R_{22}$ and $R_{23}$ are independently lower alkyl.

35. The process according to claim 22 wherein X is S-heter and heter contains 6 or 10 ring atoms and the sulfur atom is bonded to a ring carbon atom.

36. The process according to claim 22 wherein X is a nitrogen containing heteroaromatic containing 5 or 9 ring atoms and wherein X is substituted to the carbon atom bearing the $NR_{12}$ substituent through a nitrogen ring atom.

* * * * *